United States Patent [19]
Zadini et al.

[11] Patent Number: 5,415,177
[45] Date of Patent: May 16, 1995

[54] AUTOMATIC GUIDE WIRE PLACEMENT DEVICE FOR INTRAVASCULAR CATHETERS

[76] Inventors: Filiberto P. Zadini, 16814 Rayen St., North Hills, Calif. 91343; Giorgio C. Zadini, 2237 Hilltop La., Camarillo, Calif. 93012

[21] Appl. No.: 999,353

[22] Filed: Dec. 31, 1992

[51] Int. Cl.6 ............................................. A61B 5/00
[52] U.S. Cl. ................................................. 128/772
[58] Field of Search ................... 128/657, 658, 772; 604/95, 165–168, 280

[56] References Cited

U.S. PATENT DOCUMENTS

| | | | |
|---|---|---|---|
| 4,917,094 | 4/1990 | Lynch et al. | 128/657 |
| 5,161,534 | 11/1992 | Berthiaume | 128/657 |
| 5,228,452 | 7/1993 | Saron | 128/657 |
| 5,243,997 | 9/1993 | Uflacker et al. | 128/772 |

*Primary Examiner*—Max Hindenburg

[57] ABSTRACT

A guidewire placement device for intravascular catheters comprising a guidewire, a hollow needle and self-propelled means for moving said guidewire to an advanced position upon penetration of the wall of a blood vessel by the needle. The self-propelling means may be actuated manually or may include means for sensing penetration of a blood vessel by the needle and for automatically advancing the guidewire in response to such penetration.

81 Claims, 19 Drawing Sheets

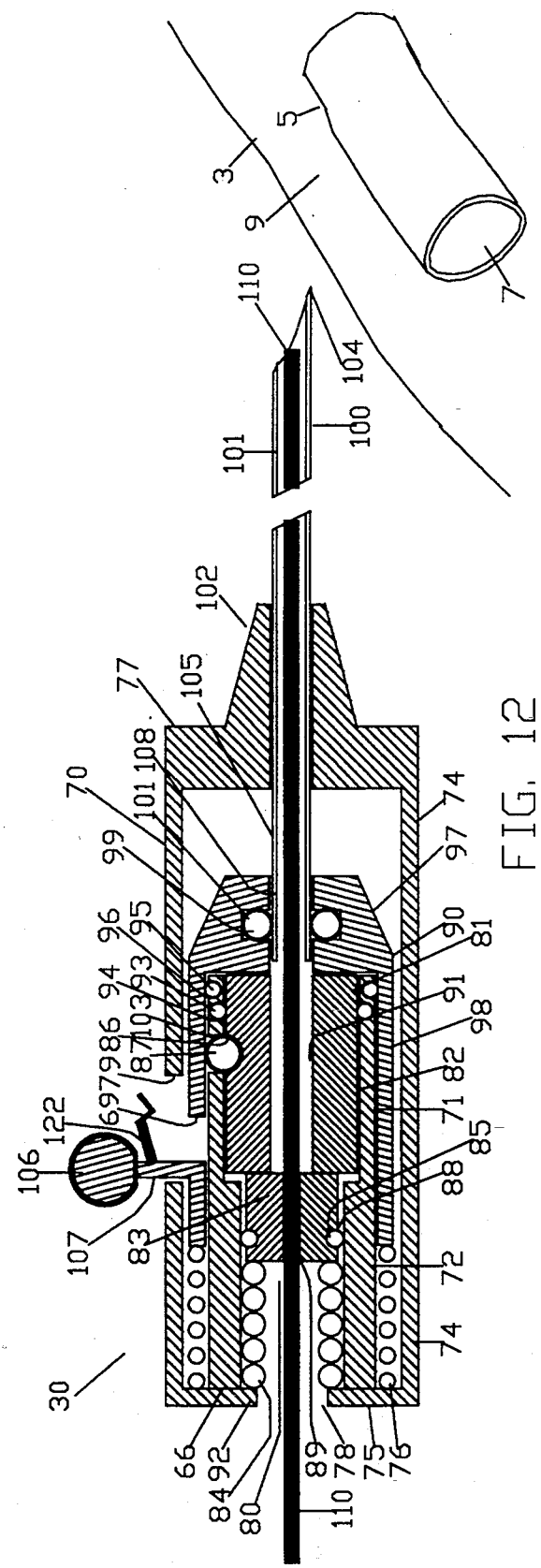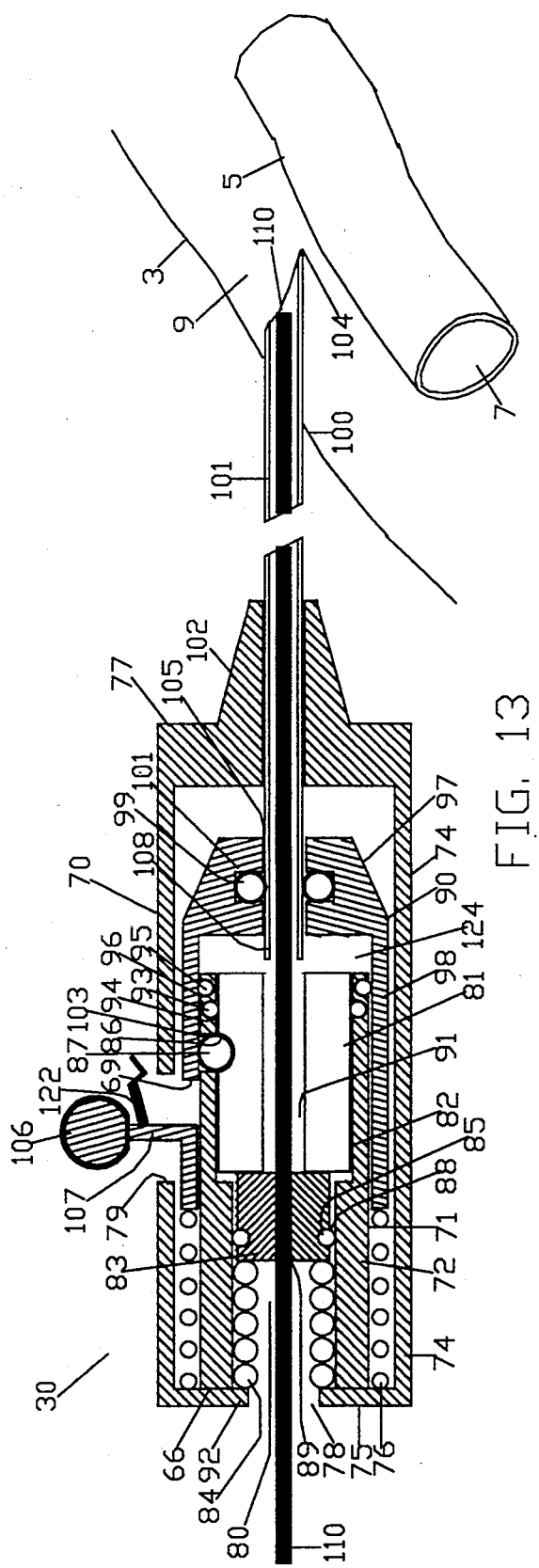
FIG. 12
FIG. 13

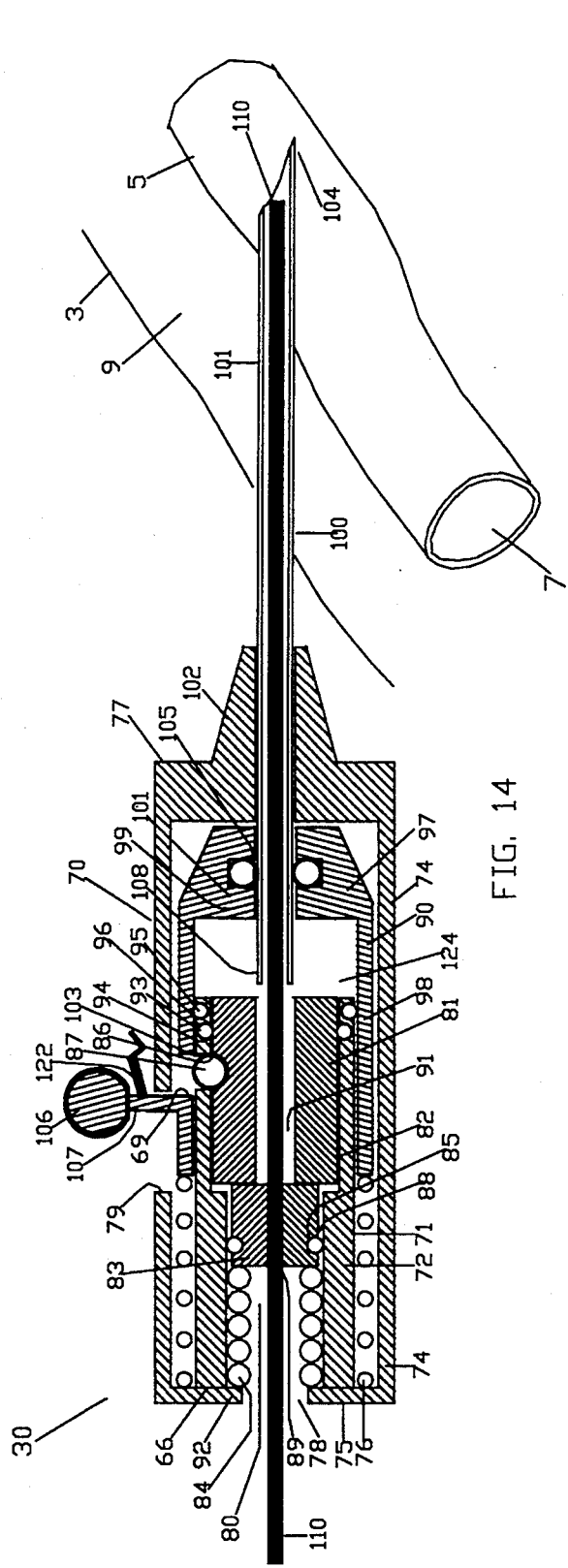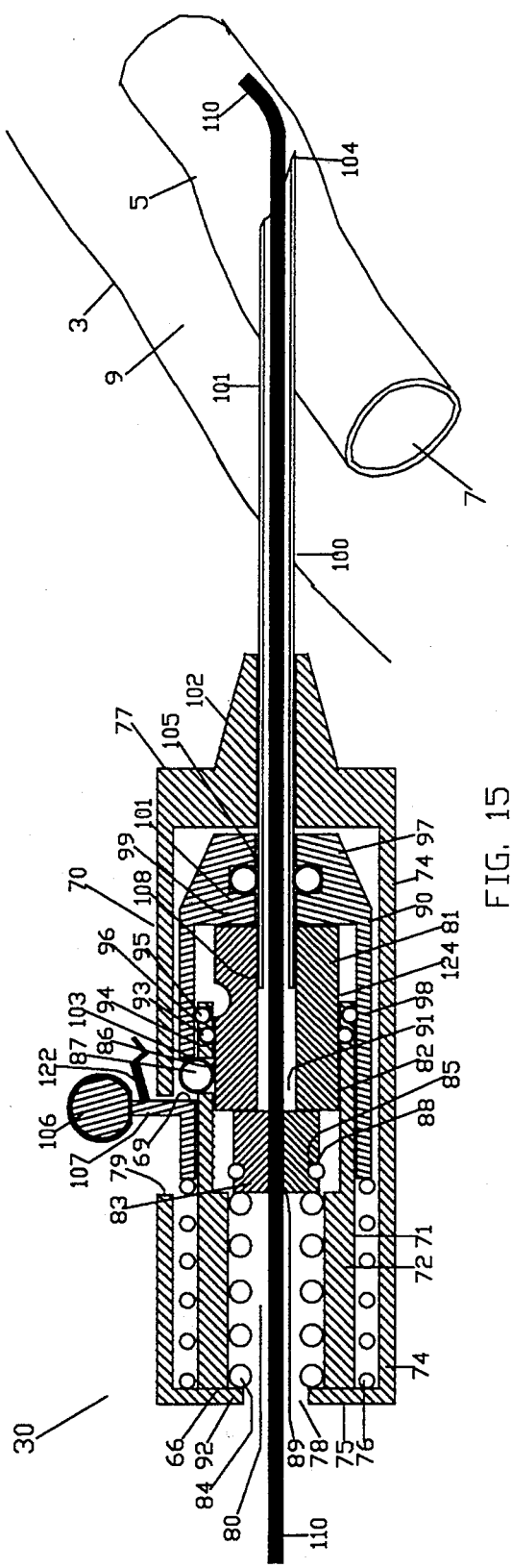

AUTOMATIC GUIDE WIRE PLACEMENT DEVICE FOR INTRAVASCULAR CATHETERS

BACKGROUND OF THE INVENTION

1. Field of the Invention

The present invention relates to intravascular wire guided catheters and specifically to automatic means of placement of a guide wire of an intravascular catheter within the lumen of blood vessels, either automatically or manually triggered by the operator.

2. Prior Art

Placing intravascular catheters within blood vessels is a common medical surgical procedure. Various types of catheters are available today to the practicing health care worker. A common type of catheter is the so called wire guided catheter based on the Seldinger technique of insertion. Such a catheter comprises a guide wire which is introduced manually into the vessel prior to the introduction of the catheter itself. The procedure is carried out as follows:

The vessel is penetrated with a hollow needle. As soon as the operator realizes that the wall of the vessel has been penetrated and the tip of the needle is within the blood vessel lumen, he or she advances the guide wire manually sliding it inside the hollow needle into the blood vessel. Once the guide wire is placed within the vessel to a desired length, the operator slides the catheter over the guide wire placing so the catheter well within the vessel lumen. This operation of sliding the catheter over the guide wire is accomplished in certain type of catheter by removing the needle and so leaving only the guide wire within the blood vessel prior to the introduction of the catheter. In other types the needle needs not to be removed prior to the sliding of the catheter over the guidewire. In all situations however the guide wire is advanced within the vessel lumen manually by the operator once the occurred penetration of the blood vessel by the hollow needle has been ascertained.

Various are the reasons of failure in this manual procedure of guide wire placement within the blood vessel lumen. The operator can fail because many factors such as inability to recognize penetration of the blood vessel well, sequence delays, disruption of the continuity of the blood vessel, patient anatomical variability etc.

A search in the patent office has revealed no prior art in this specific field i.e. in automatic guide wire placement within a blood vessel.

SUMMARY OF THE INVENTION

The disadvantages of manual guide wire placement within the blood vessels are overcome with the present invention and an automatic guide wire placement device is proposed which automatically advances the guide wire, once the blood vessel has been penetrated and which may be triggered one handedly or, in a preferred embodiment, includes means for sensing penetration of a blood vessel and for automatically advancing the guide wire in response to such penetration.

The advantages of the present invention are preferably attained by providing an improved guide wire placement device comprising a needle, a guide wire, means urging said guide wire to an advanced position and means for triggering the guide wire advancing means upon penetration of a blood vessel. The triggering means may be manual or may include means for sensing penetration of a blood vessel and for automatically advancing the guide wire in response to such penetration.

Accordingly it is an object of the present invention to provide an improved guide wire placement device.

Another object of the present invention is to provide an improved guide wire placement device which permits one handed insertion and placement of a guide wire within a blood vessel.

An additional object of the present invention is to provide an improved guide wire placement device which permits automatic advancement of the guide wire once a blood vessel has been penetrated.

A specific object of the present invention is to provide an improved guide wire placement device comprising an hollow needle, a guide wire, means urging said guide wire to an advanced position and means for triggering the guide wire advancing means upon penetration of the wall of the blood vessel. The triggering means may be manually operated or may include means for sensing penetration of a blood vessel and for automatically advancing the guidewire in response to such penetration.

These and other objects and features of the present invention will be apparent from the following detailed description, taken with reference to the figures of the accompanying drawings.

BRIEF DESCRIPTION OF THE DRAWINGS

FIG. 12 is a view of the device of FIG. 10 in a fully armed condition prior to skin penetration.

FIG. 13 is a view of the device of FIG. 10 after penetration of the skin by the needle but prior to vessel penetration.

FIG. 14 is a view of the device of FIG. 10 just after blood vessel penetration by the needle.

FIG. 15 is a view of the device of FIG. 10 showing the automatic guide wire advancement within the blood vessel.

DESCRIPTION OF THE INVENTION

Figure 1:
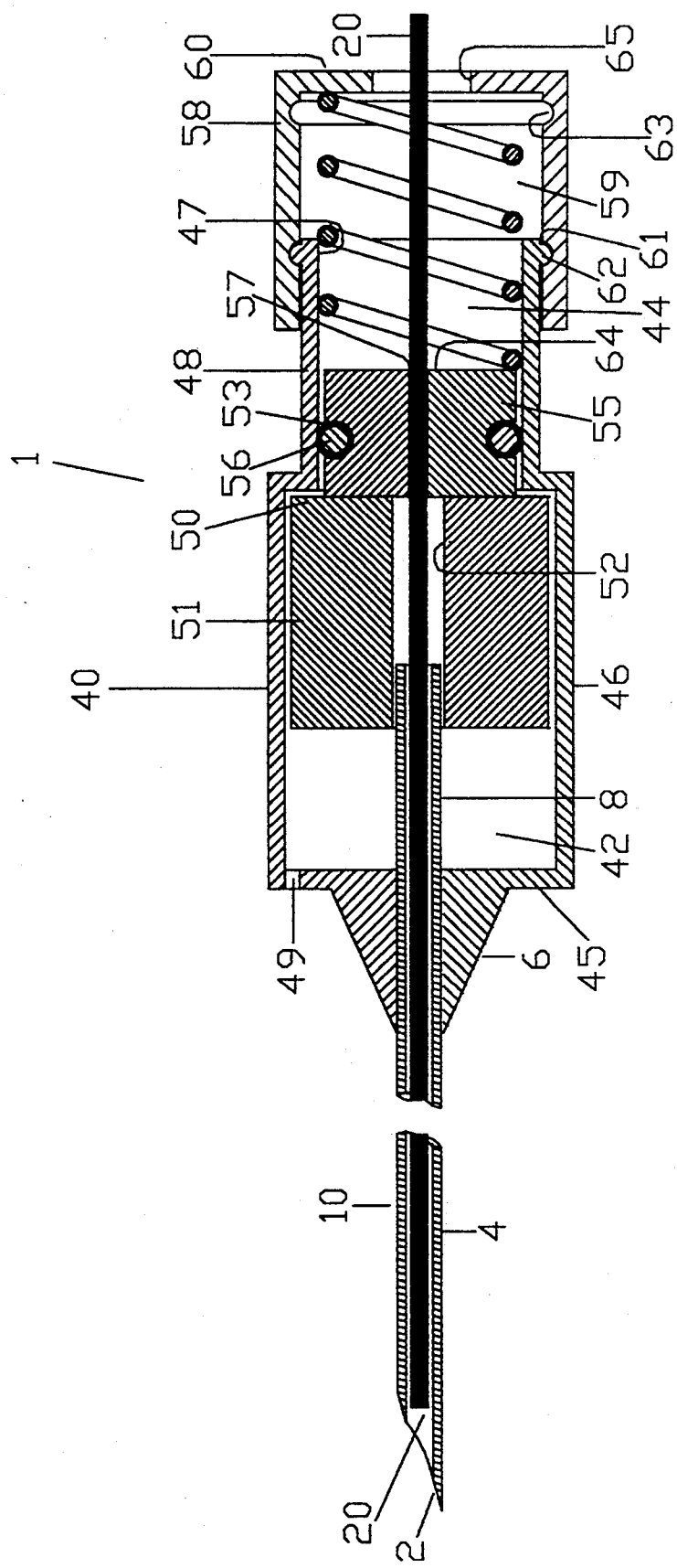
FIG. 1 a cross sectional view through the guide wire placement device prior to use, embodying the present invention.

In that form of the present invention chosen for the purpose of the illustration in FIG. 1 a guide wire placement device indicated generally at 1 is shown comprising three main parts: a needle 10, a guide wire 20 and an introducer or inserter unit or housing unit 40. Needle 10 is of hollow tubular shape, having pointed tip 2, shaft 4, needle hub 6 and posterior needle segment 8 contained whithin anterior chamber 42 of housing unit or introducer member 40 as it will be evident from the description below. Housing unit or introducer member 40 of general hollow cylindrical shape is composed of two chambers of different diameter: anterior chamber 42 of larger diameter or expanded and chamber 44 of smaller diameter or narrowed, situated posteriorly and in continuity with anterior chamber 42. Anterior chamber 42 is delimited laterally by wall 46, anteriorly by walls 45, fused with needle hub 6 of needle 10 and posteriorly is in continuity with posterior chamber 44. Posterior needle segment or tubular guide 8 is located in chamber 42 and puts in communication hollow needle 2 with said chamber. Small window 49 is located on anterior wall 45 of anterior chamber 42, above needle hub 6 of needle 10 and puts in communication anterior chamber 42 with the exterior. Posterior chamber 44, delimited laterally by walls 48 is open posteriorly via opening 47. Piston 50 is contained whithin introducer member 40 and is composed of two segments, anterior segment 51 with tunnel 52 at its center along its longitudinal axis, contained whithin anterior chamber 42 and posterior segment 55 or releasable gripping means of smaller diameter contained in posterior chamber 44 of introducer member 40. Whithin tunnel 52 of anterior piston segment 51 is harbored a small portion of posterior needle segment or tubular guide 8.

Posterior piston segment 55 of piston 50 is a releasable gripping means, made of resilient compressible material such as a rubber compound, and mounted with expanding "O" ring 56, made of resilient material such a steel, seating on annular recess 53 of posterior piston segment 55. In position of rest prior to use, "O" ring 56 will constrict the compressible posterior piston segment 55 around guide wire 40, exerting so a firm grip on it, along axial tract 57 due to the inability to expand of metal "O" ring whithin the rigid walls 48 of posterior chamber 44. "O" ring 56 also provides a low friction sliding interface between the rigid wall 48 of posterior chamber 44 and compressible posterior piston segment 55.

Guide wire 20 is loosely encircled by hollow needle 10 from its very tip 2 to posterior needle segment 8 to permit the passage of blood around its surface. Guide wire 20 continues posteriorly through introducer chambers 42 and 44, axially running through anterior piston segment tunnel 52 and axial tract 57 of posterior piston segment 55. It exits posteriorly through opening 47 of posterior chamber 44, opening 65 of cylindrical sliding cap 58, described below and continues to a desired length. Posteriorly, cylindrical sliding cap or arming member 58 is mounted concentrically on outer surface of walls 48 of posterior chamber 44 of introducer member or housing 40. Cap or arming member 58 is slideable over walls 48 of posterior chamber 44 and in position of rest prior to use is extended posteriorly by the action of the means for advancement or self propulsion, spring 59 on circular flange 60 of cap 58. On inner surface of cap 58 are anteriorly annular recess 61 and posteriorly annular recess 63. Spring 59 rests anteriorly on posterior surface 64 of posterior piston segment 55 and posteriorly, as just stated, on flanges 60 of slideable cap 58. Annular recess 61 on inner surface of cap 58 seats in position of rest prior to use on corresponding annular arrest or rim or collar 62 of walls 48 of posterior introducer chamber 44 not allowing further posterior displacement and exit of cap 58 from posterior introducer chamber 44. Sliding cylindrical cap or arming member cap 58 is open posteriorly via opening 65 to permit the passage of guide wire 20.

Figure 2:
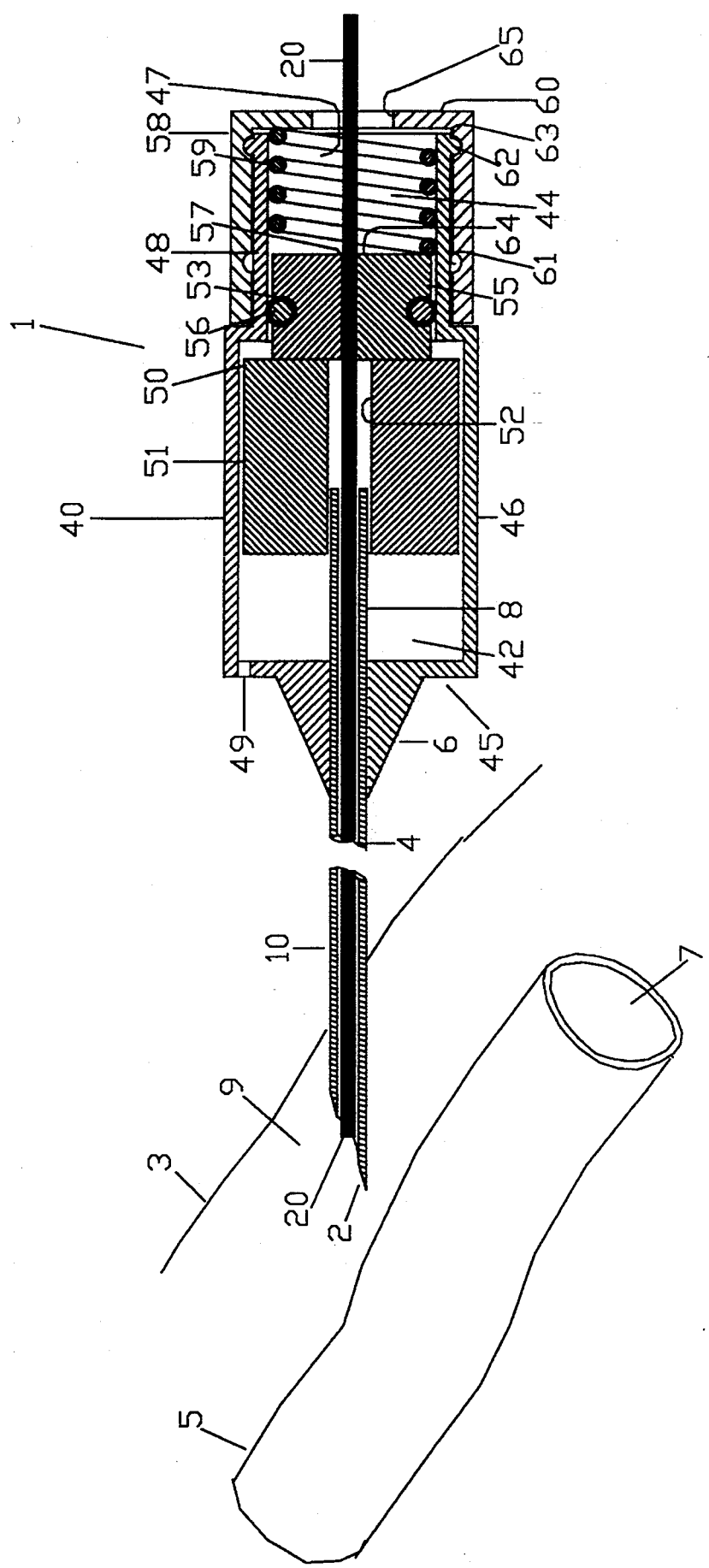
FIG. 2 shows the device of FIG. 1 in armed condition, ready to be used, after skin penetration but prior to vessel penetration.
Figure 3:
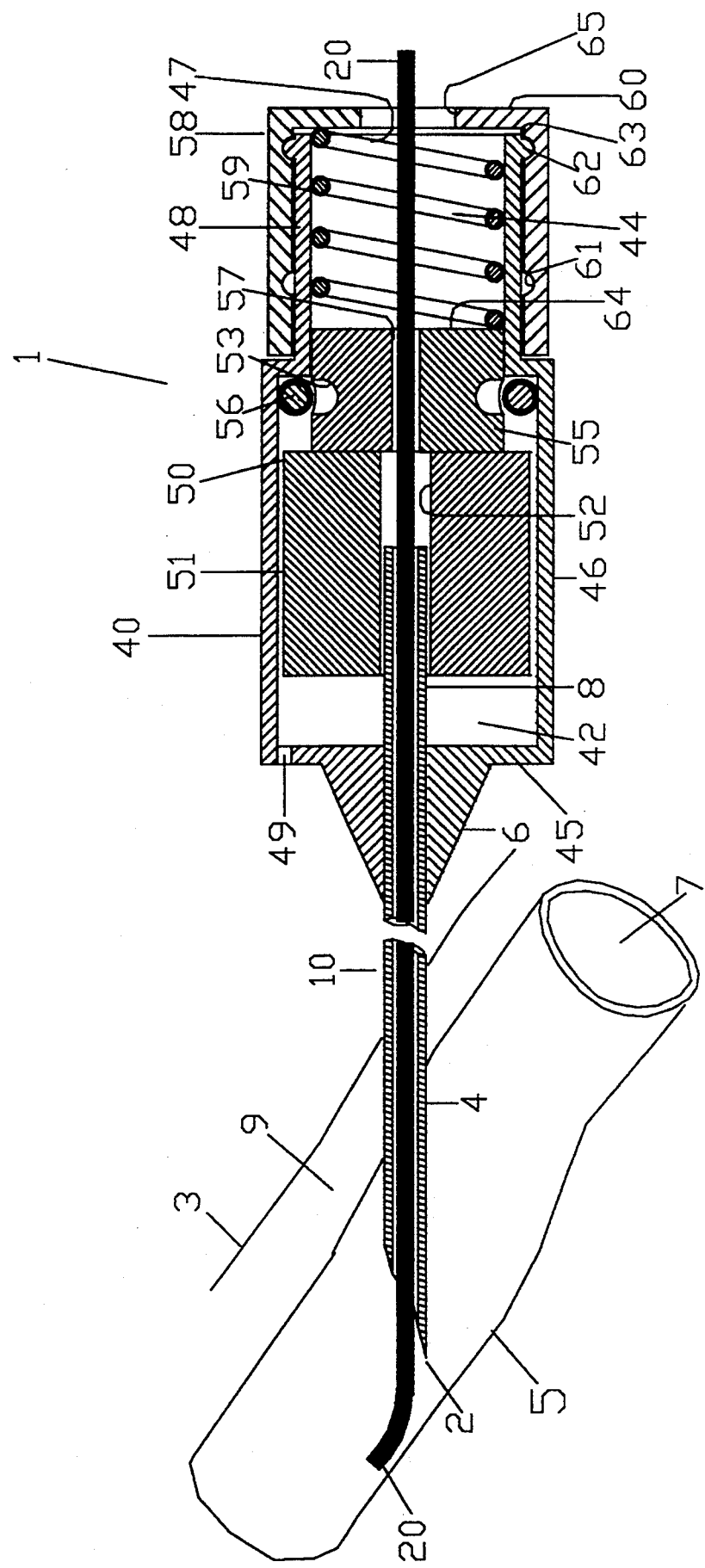
FIG. 3 shows the device of FIG. 1 after blood vessel penetration with the guide wire advanced within the blood vessel.
Figure 5:
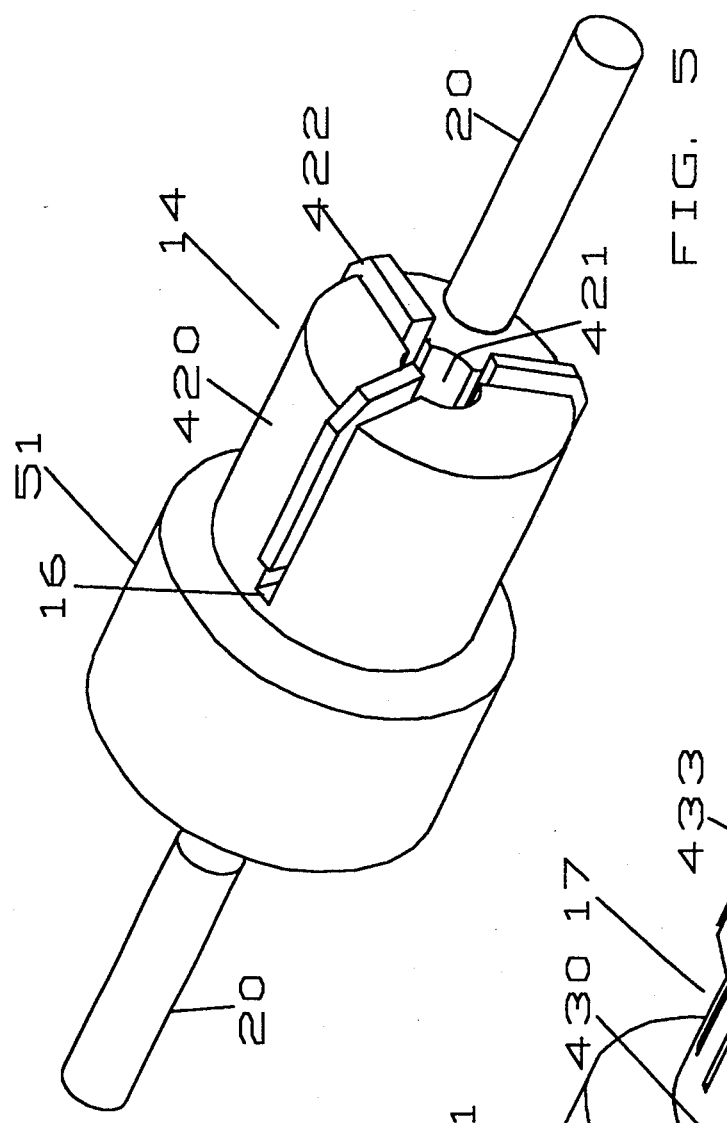
FIG. 5 is a perspective view of an alternative form of the engage/release mechanism of the guide wire described in the previous figures, specifically a jaw chuck.

FIG. 5 is a perspective view of an alternative form of the guide wire engage/release mechanism or gripping means of FIGS. 1 to 3, specifically a three-jaw chuck. Jaw chuck 14 substitutes in its location and function, posterior piston segment 55. Jaw chuck 14 is composed of supporting piston member 420 with three radially equidistant linear slots 16 where jaws 422 are slideably mounted. Supporting piston member 420 is attached to anterior piston member 51 as described for posterior piston member 55. Guide wire 20 is engaged and clamped within bore 421 of jaw-chuck 14 by jaws 422, constricted around guide wire 20 by the rigid walls 48 of chamber 44, when jaw chuck 14 is in chamber 44, prior to use of the device.

Figure 6:
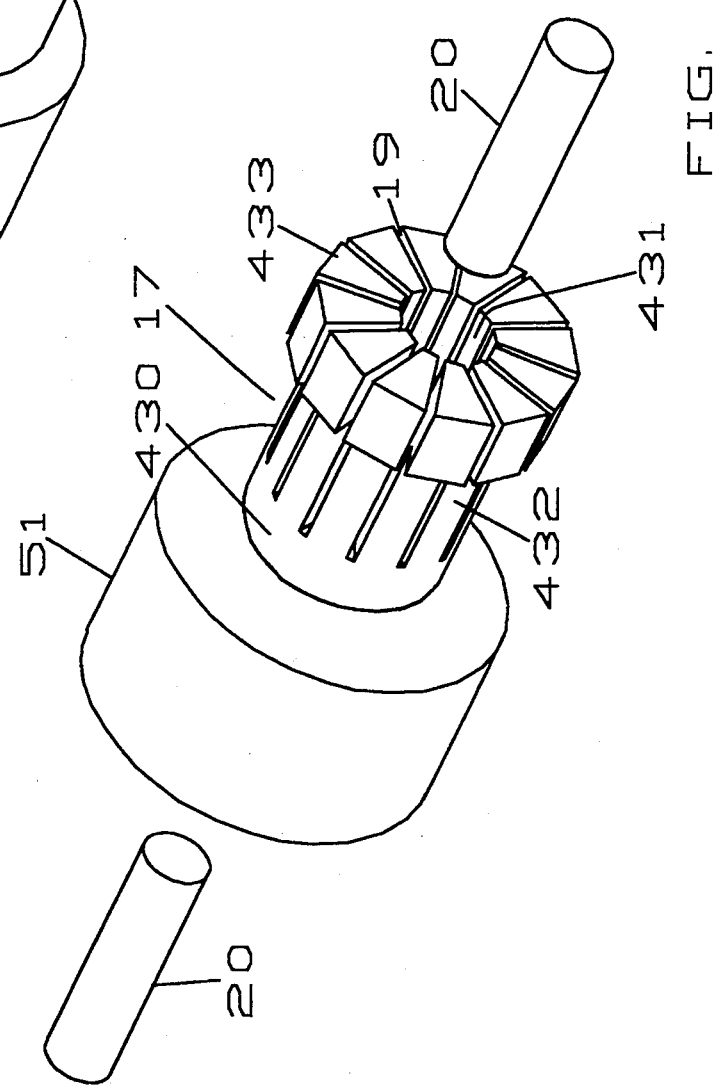
FIG. 6 is a perspective view of yet an alternative form of the engage/release mechanism of the guide wire described in the previous figures, specifically a mandrel.

FIG. 6 is a perspective view of yet an alternative form of the guide wire engage/release mechanism or gripping means of FIG. 1 to, specifically a mandrel. Mandrel or gripping unit 17 substitutes in location and function posterior piston segment 55. It is a cylindrical piston like structure formed with multiple resilient gripping arms or bars 432, equidistant from bore 431, protruding from piston base 430. Guide wire 20 is engaged and clamped, with the device in position of rest prior to use, at the center of mandrel 17, along its bore 431, by gripping bars or arms heads 433 constricted centripetally by the rigid walls 48 of chamber 44.

DESCRIPTION OF THE OPERATION

In use, the operator holding the device with one hand, first penetrates the skin 3 of the patient with needle tip 2 of needle 10 in a area of a visible or expected location of vessel, artery, vein or body cavity or organ. As shown in FIG. 2 when needle tip 2 is well under the skin 3, the operator arms the device by pushing forward cap 58 sliding it over outer surface of walls 48 of posterior introducer chamber 44 overcoming the initial little resistance offered by annular arrest or rim or collar 62 of walls 48 of posterior chamber 44, seating on corresponding annular recess 61 of cap 58. Annular arrest or rim or collar 62 will engage annular recess 63 locking so cap 58 in advanced position. Spring 59 will be then compressed between posterior surface 64 of posterior piston segment 55 and circular flanges 60 of advanced cap 58. Piston 50 will be not allowed to be displaced anteriorly by the action of spring 59 due to the inability of guide wire 20 to advance due to the opposing resistance offered by the subcutaneous tissues 9 to the guide wire tip, guide wire 20 being urged forward by piston 50, more precisely by its posterior segment 55 which engages guide wire 20 by consricting around it by the action of expanding "O" ring 56, constrained on its turn by the rigid walls 48 of posterior chamber 44.

Figure 4:
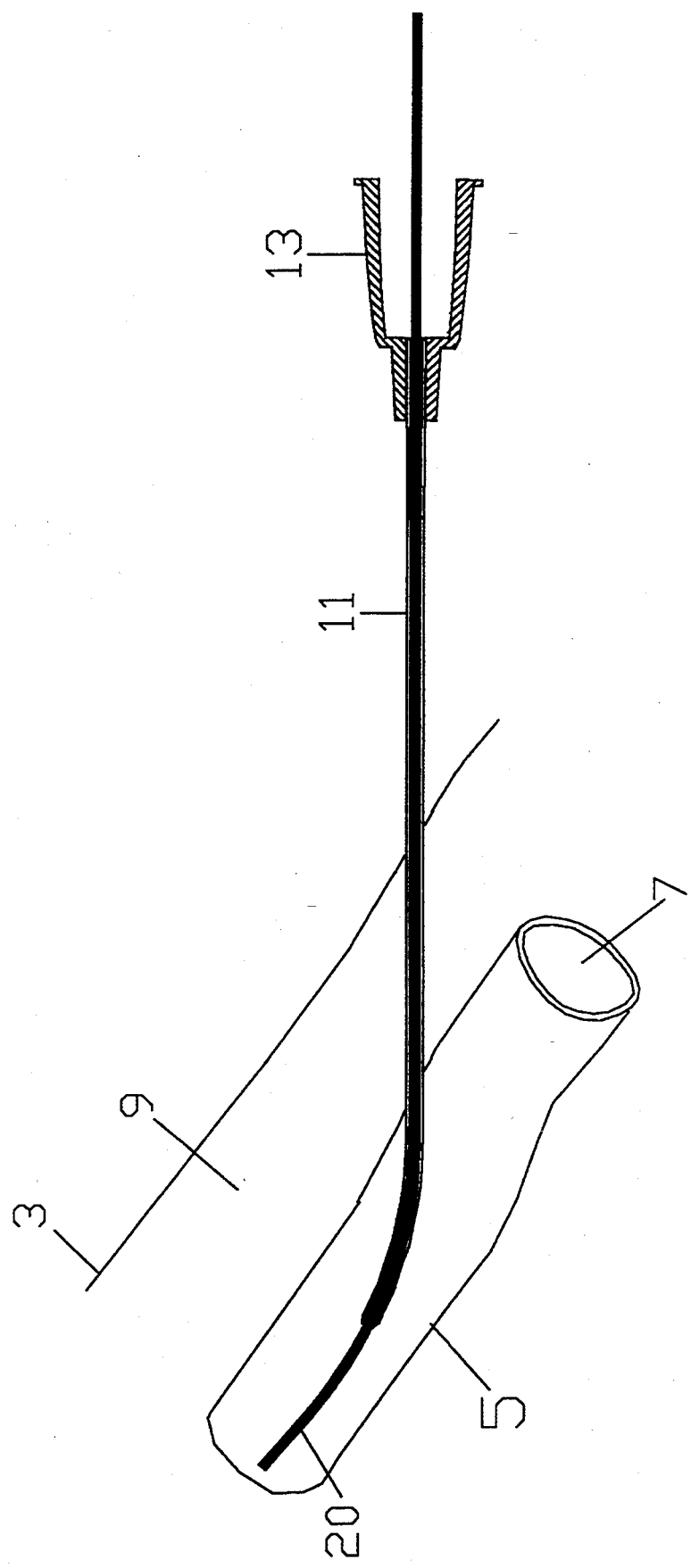
FIG. 4 is a view of a catheter advanced over the guide wire into the vessel.

As shown in FIG. 3 when needle tip 2 of needle 10 penetrates into the interior or lumen 7 of a blood vessel 5, such action is a triggering mechanism for the advancing means or spring 59. Guide wire 20, no longer retained by the subcutaneous tissues 9 will advance whithin the lumen 7 of the vessel being urged forwardly, as stated, by posterior piston segment 55 gripping guide wire 20, by the action of spring 59 on posterior surface 64 of posterior piston segment 55. Posterior piston segment 55 of piston 50 will thus enter enterior introducer chamber 42 of larger diameter than chamber 44. Advancement of piston 50 will be guided by the sliding of tunnel 52 of anteriotr piston segment 51 over tubular guide or posterior needle segment 8. In chamber 42 posterior piston segment 55 will be able to rapidly expand as metal "O" ring 56 moved anteriorly with it is also allowed to expand and will no longer costrict posterior piston segment 55. This expension of the compressible posterior piston segment 55 will result in releasing the grip around guide wire 20 along axial tract 57, disengaging guide wire 20 from piston 55. Guide wire 20 thus will not advance further. At this point the operator may extract the device sliding it posteriorly over guidewire 20 for the whole length of the guide wire 20 or may further advances the guide wire 20 manually within the vessel lumen 7 and then will extract the device. Guide wire 20 will be left in place whithin the vessel lumen 7 and a catheter 11 of adequate size will be slided over it and advanced within the vessel lumen 7 as shown in FIG. 4. Then the operator holding the catheter 11 with one hand, within the vessel lumen 7, will extract guide wire 20 with the other hand, leaving whithin the vessel lumen 7 only the catheter 11.

Jaw-chuck 420, shown in FIG. 5, can replace functionally posterior piston segment 55. When jaw-chuck 420, urged forward by spring 59, will enter enterior chamber 42, of larger diameter, jaws 422, no longer constricted by the rigid walls 48 of posterior chamber 44, will release the grip on guide wire 20, as described for the device of FIG. 1.

Similar mechanism and function is accomplished by mandrel 430 shown in FIG. 6. When mandrel 430, urged forward by spring 59 will enter anterior introducer chamber 42 carrying forward guide wire 20, resilient gripping arms or bars 432, now no longer constricted by the rigid walls 48 of posterior chamber 44, will release the grip on guide wire 20.

Figure 7:
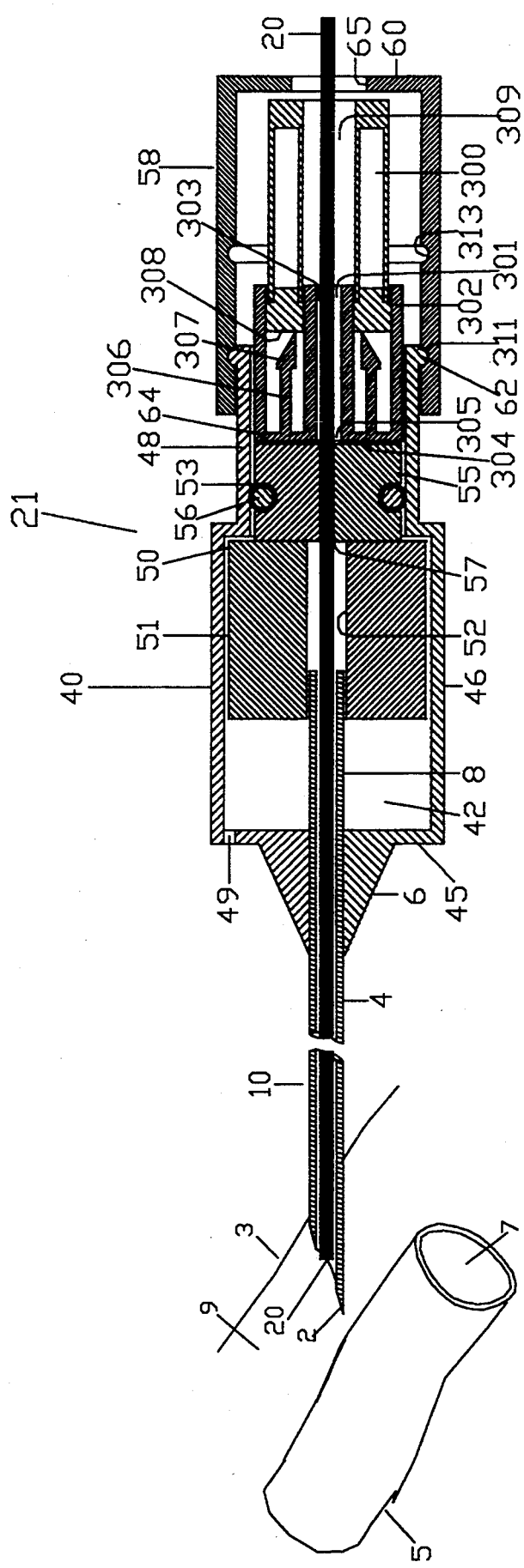
FIG. 7 is a cross sectional view of a different version of the device of FIG. 1, in which the guide wire is advanced by pneumatic means. The device is shown after skin penetration in unarmed condition.
Figure 8:
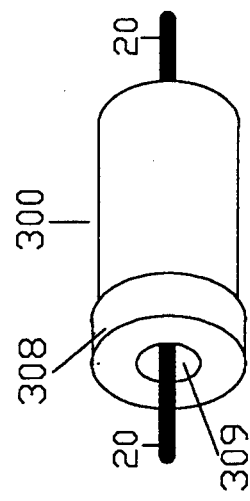
FIG. 8 shows isolated the pneumatic cylinder of FIG. 7.

FIGS. 7 and 8 describe a device that is essentially similar to the device described on FIGS. 1 to 3 with the difference that the guide wire is advanced by pneumatic means and not by spring. In this version spring 59 is no longer present and it has been substituted by tunnelled pneumatic cylinder 300 containing compressed air, shown in isolated form in FIG. 8. Tunnelled pneumatic cylinder 300 is located posteriorly to introducer unit 40, surrounded laterally and posteriorly in position of rest prior to use by sliding cap 58. Its anterior segment is partially contained whithin intermediate cylinder 302 as it will be evident from the description below. Intermediate cylinder 302 is interposed between tunnelled pneumatic cylinder 300 and posterior piston segment 55 resting with its base 304 on posterior surface 64 of posterior piston segment 55. Intermediate cylinder 302 has at its center, along its axis tunnel 303 for the whole lenght extending from opening 305 of base 304 to posterior opening 301, to permit the unobstructed passage of guide wire 20. Perforating solid needles 306 are also attached to base 304 of cylinder 302 being needle tips 307 in contact with circular sealing cap 308, preferably made of a rubber compound, of tunnelled pneumatic cylinder 300. Pneumatic tunnelled cylinder 300 is slideable in air tight fashion due to circular sealing cap 308 whithin intermediate cylinder 302. Guide wire 20 passes unobstructed, as stated, whithin tunnel 303 of intermediate cylinder 302 to continue trough tunnel 309 of pneumatic cylinder 300 and then exit trough opening 65 of sliding cap 58 to continue to a desired length.

Sliding cap 58 is basically the same as the one described for the device of FIGS. 1 to 3 except that annular recesses 311 and 313 replace recesses 61 and 63.

DESCRIPTION OF THE OPERATION

The device is basically operated as the device of FIGS. 1 to with the following differences:

Once skin 3 is penetrated by needle tip 2 and prior to vessel 5 penetration, as described for the device of FIG. 1, the operator will press forward sliding cap 58 until sliding cap 58 will be locked by the engaging of circular arrest 62 on posterior annular recess 313. The advancement of tunnelled pneumatic cylinder 300 urged forward by the advancing of circular flanges 60 of sliding cap 58 will cause perforation by solid needles 306 of sealing cap 308 of pneumatic cylinder 300, with resulting air escape from pneumatic cylinder 300 into intermediate cylinder 302. Compressed air, due to the air tightness between pneumatic cylinder sealing cap 308 and the interior of walls 28 of intermediate cylinder 302, will urge forward intermediate cylinder 302 which, on its turn, will urge forward piston 50 acting upon posterior surface 64 of posterior piston segment 55. Piston 50 will be unable to advance and with it guide wire 20, gripped by posterior piston segment 55, due to the resistence offered by the subcutaneous tissue 9. Once blood vessel 5 will be penetrated by needle tip 2, forwardly urged posterior piston segment 55 will carry forward a small segment of guide wire 20 whithin the vessel lumen 7 exactly in the same manner described for the device of FIG. 1. Posterior piston segment 55 will release its grip on guide wire 20 once it will enter anterior chamber 42 as described for the device of FIG. 1. The following operational steps are exactly the same as the one described for the previous device.

Figure 9:
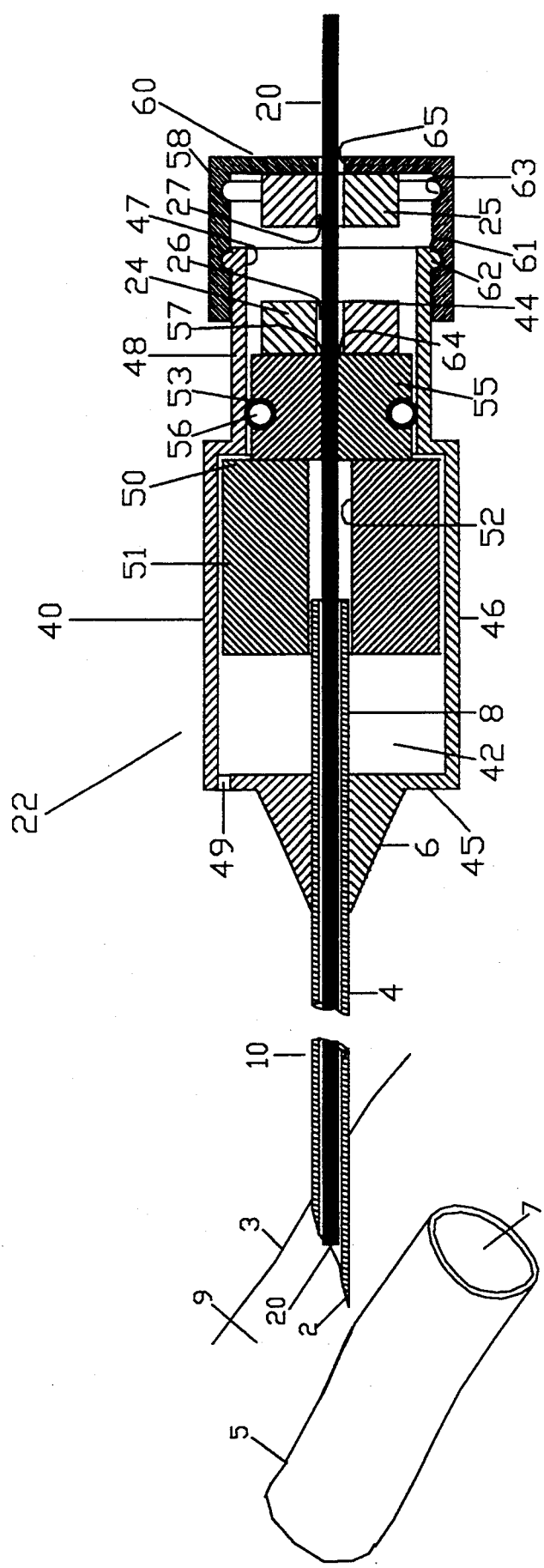
FIG. 9 is a cross sectional view of a different version of the device of FIG. 1 in which the guide wire is advanced by magnetic means. The device is shown after skin penetration in unarmed condition.

FIG. 9 shows an alternative form of the device of FIG. 1 essentially similar to it with the difference that the guide wire is self propelling or advancing by magnetic means, in this version spring 59 no longer present is substituted by anterior magnet 24 and posterior manget 25 facing each other with opposing polarities. Anterior magnet 24 of general cylindrical shape with at its center tunnel 26, seats and is attached to posterior surface 64 of posterior piston segment 55. Posterior magnet 25, of same cylindrical shape, with tunnel 27 at its center, seats and is attached to the interior of flanges 60 of sliding cap 58. Guide wire 20 exiting from axial tract 57 of posterior piston segment 55 passes through tunnel 26 and 27 respectively of manets 24 and 25, to continue posteriorly through opening 65 to a desired length.

DESCRIPTION OF THE OPERATION

In operation, the operator, after inserting needle tip 2 under skin 3 of a patient, will arm the device pushing forward cap 58 until cap 58 will lock anteriorly by the engaging of circular arrest or rim or collar 62 on circular recess 63. Despite the reciprocal magnetic repulsion of magnet 24 and 25, advancement of piston 50 and guide wire 20 carried by posterior piston segment 55 due to the same gripping releasing means described for the device of FIG. 1, will not occur due to the opposing resistence offered by the subcutaneous tissues 9 to guide wire 20.

Once blood vessel 5 will be penetrated by needle tip 2, guide wire 20 will be able to advance within the vessel lumen 7 as described for the previous device of FIG. 1. The following operational steps are the same as the ones described for the device of FIG. 1.

Figure 10:
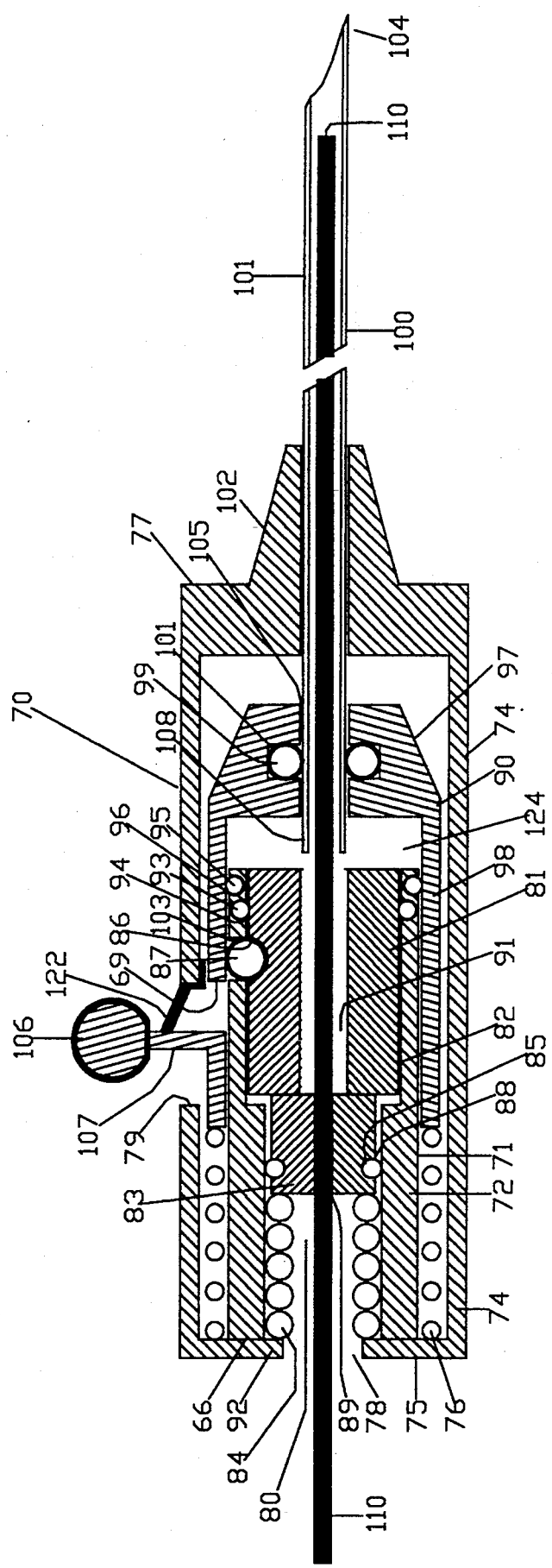
FIG. 10 is a cross sectional view trough line 118—118 of FIG. 11 showing an alternative form of the device, fully automatic, prior to use.

FIGS. 10 to 16 show an alternative form, fully automatic, of the device of FIG. 1, in which a vacuum is automatically created in the device and the guide wire is automatically advanced in response to blood vessel penetration. As shown in FIG. 10, in this version, the automatic guide wire placement device, generally indicated at 30, is composed of four main parts: support case or housing 70, sliding vacuum cylinder or cap 90, hollow needle 100 and guide wire 110.

Support case or housing 70 is of generally hollow cylindrical shape. It is delimited laterally by side walls 74, anteriorly by wall 77 fused with needle hub 102, posteriorly by wall 75 with flanges 92 surrounding opening 78 where guide wire 110 exits and continues to a desired length as it will be evident from the description below. Within housing or support unit 70 is concentrically mounted piston case 72 open anteriorly and attached posteriorly with base 66 to posterior well 75 of support unit or housing 70 surrounding opening 78 of posterior well 75 of housing unit 70. Chamber 80, delimited laterally by wall 71 of piston case 72 and anteriorly by vacuum cap or cylinder 90 is of smaller diameter on its posterior half, being wall 71 thicker on its posterior half. Vacuum space or chamber 124 is the space within chamber 80 in front of anterior piston segment 81 as it will be described in detail below. Side wall 71 of piston case 72 is formed with round window 103 housing upper portion of locking ball 87. Within piston case 72 is contained piston 82 composed of anterior segment 81 and posterior segment 83 of smaller diameter. Anterior piston segment 81 with tunnel 91 along its central longitudinal axis to permit the unobstructed passage of guide wire 110, is formed with annular recess 86 housing the lower portion locking ball 87 in position of rest prior to use. Posterior piston segment 83 is contained in the posterior narrower segment of chamber 80. It is of smaller diameter then anterior piston segment 81, is made of resilient material such as a rubber compound and is mounted with expanding "O" ring 88 made of resilient compressible material such as steel, as explained for the device of FIG. 1. "O" ring 88 seats on annular recess 85 of posterior piston segment 83. In position of rest prior to use, resilient expanding ring 88 will costrict compressible posterior piston segment 83, exerting and maintaining a firm grip on guide wire 110 along axial tract 89 located at the center of posterior piston segment 83.

Self propelling, advancing, biasing means or spring 84 is mounted posteriorly between posterior piston segment 83 and circular flanges 92 of posterior wall 75 of support case 70 exerting forward pressure on posterior piston segment 83. Side walls 71 of piston case or inner cylinder 72, have on its anterior segment two "O" rings: 93 and 95 contained respectively in circular groves 94 and 96. "O" ring 93 maintains air tightness between walls 71 of piston case 72 and anterior piston segment 83 and "O" ring 95 maintain air tightness between walls 71 of piston case 72 and walls 98 of vacuum cap 90.

Figure 11:
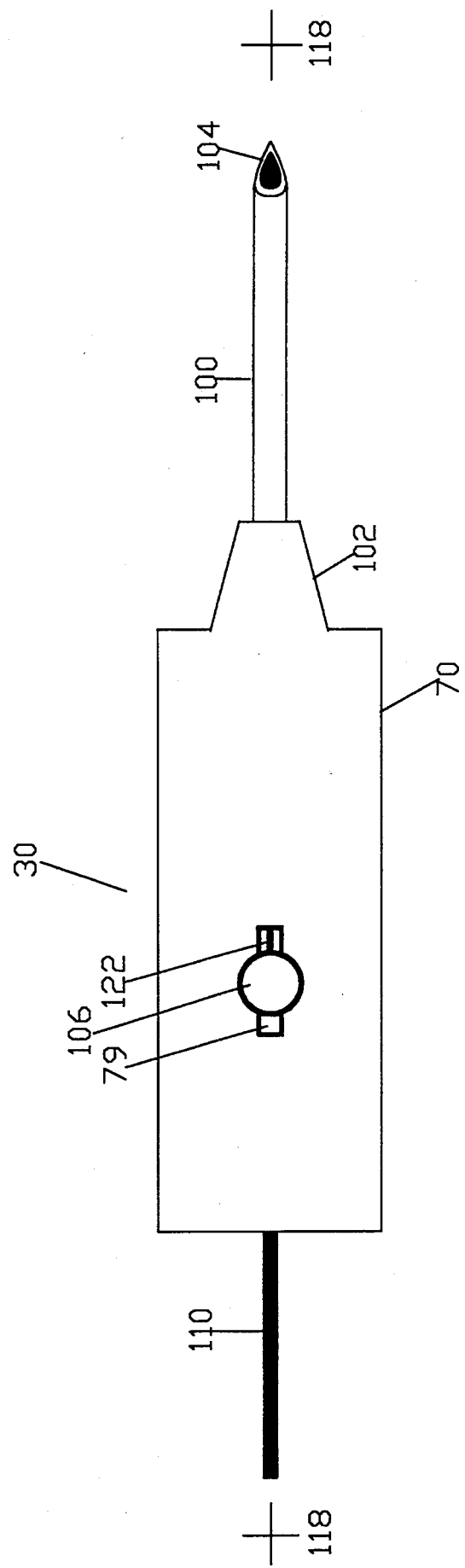
FIG. 11 is a top view of the device of FIG. 10.

Between side walls 71 of piston case 72 and side walls 74 of support case or housing 70 are interposed from front to back vacuum cylinder or cap 90 slideable between the two and, posteriorly, spring 76 resting on posterior wall 75 of support case 70. As better shown in FIG. 11, side wall 74 of support case 70 presents superiorly slot 79 through which knob 106 with its stalk or shaft 107 exits. As shown in FIG. 10 and 11 attached to stalk 107 is resilient arrest 122 for vacuum cylinder or cap 90. Vacuum space or chamber 124 of chamber 80 is the space in front of anterior piston segment 81 delimited with the device in position of rest prior to use laterally by side wall 98 of vacuum cylinder 90, anteriorly by anterior segment 97 of vacuum cylinder 90 and posteriorly by surface 109 of anterior piston segment 81.

Vacuum cylinder or cap 90 is of hollow cylindrical shape having side wall 98 and anterior segment 97. It is slideably mounted between side wall 74 of support case or housing 70 and wall 71 of piston case 72. Anterior segment 97 has at its center axial tract 105 which harbors posterior needle segment 108, in a slideable fashion protruding in vacuum chamber or space 124. "O" ring 99, seating in grove 101 of anterior segment 97 of vacuum cap 90, ensures air titghtness between posterior needle segment 108 and anterior segment 97 of vacuum cap 90. Air tightness is maintained between vacuum cap 90 and piston case 72 while air passage is permitted between vacuum cap 90 and support case wall 74. Round window 69 is formed in side wall 98 of vacuum cylinder or cap 90 just in front of knob stalk 107 and is of adequate diameter in order to permit the passage of ball 87. Ball 87 is maintained in recess 86 of anterior piston segment 81 and window 103 of side wall 71 of piston case 72 by side wall 98 of vacuum cap or cylinder 90. Spring 76 rests on posterior wall 75 of support or housing unit 70 interposed between wall 74 of support case or housing 70 and wall 71 of piston case 72. It urges forward in position of rest prior to use, vacuum cylinder or cap 90. Vacuum cap 90 is, however, unable to advance due to resilient arrest 122 releasably engaged to proximal edge of slot 79 of support case 70. Needle 100 is of hollow tubular shape, as described for the device of FIG. 1, having tip 104, shaft 101, hub 102 and posterior needle segment 108. Guide wire 110 is loosely encircled by hollow needle 100 starting at needle tip 104 continues posteriorly within tunnel 91 of anterior piston segment 81, axial tract 89 of posterior piston segment 83, exits thru opening 78 of posterior wall 75 of support member 70 to a desired length.

DESCRIPTION OF USE

As shown in FIG. 12, in use, the operator first displaces posteriorly introducer member 90 in respect of external case 70 by grabbing knob 106 or triggering mechanism and pulling it backward. This will cause the disengagement of resilient arrest 122 from support member 70 at the anterior end of slot 79 of support member 70. Vacuum chamber or space 124 will disappears due to the posterior displacement of vacuum cylinder or cap 90 in respect of anterior surface 107 of anterior piston segment 81.

Figure 16:
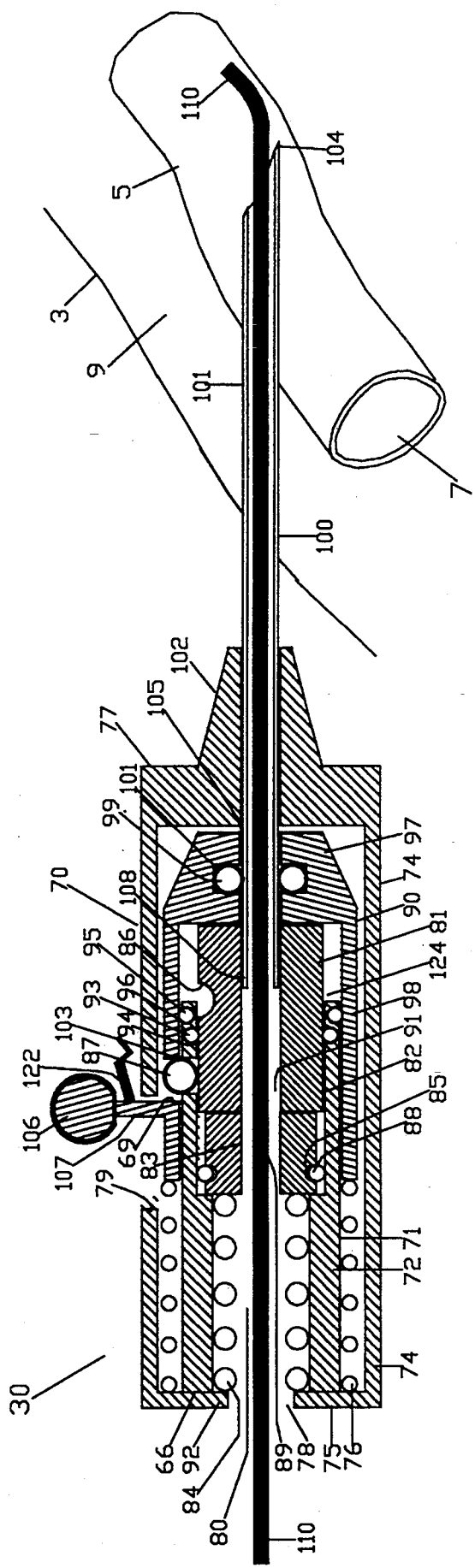
FIG. 16 is a view of the device of FIG. 10 in a further stage of operation in which the guide wire automatic advancement is completed and the guide wire is released.

As shown in FIG. 13, the operator with the device armed by holding knob 106 in backward position, keeping so vacuum cylinder or cap 90 backward against the forward action of spring 76, will penetrate skin 3 with needle tip 104. At this point, after the operator will realize that needle tip 104 is well under the skin, he or she will release knob 106. Vacuum cap 90 will be potentially free now to move forward causing so the creation of vacuum in vacuum space or chamber 124 in front of anterior surface 109 of anterior piston segment 81. However due to the sealing qualities of the subcutaneous tissue 9, vacuum cap or cylinder 90 will be permitted to move forward only by a fraction or nothing at all. When the operator will penetrate blood vessel 5 with needle tip 104, as shown in FIG. 14, blood will rush in vacuum chamber 124, in front of anterior surface 109 of anterior piston segment 81, due, as explained, to the vacuum formed by the advancement of vacuum cylinder or cap 90 in respect of anterior piston segment 81. Advancement of vacuum cap 90 will activate the means actuating the self propelled means of guide wire advancement: such an advancement will cause alignement of window 66 with ball 87 seating in annular recess 86 of anterior piston segment 81 and engaged in window 103 of side wall 71 of piston case 72. Ball 87, no longer retained in recess 86 by side wall 98 of vacuum cap 90, will be forced out from recess 86 of anterior piston segment 81 by the posterior edge of recess 86 of anterior piston member 81 pressing upon the lower half of locking ball 87, being anterior piston segment 81 urged forward by spring 84 acting upon posterior piston segment 83, thus unlocking piston 81 from piston case 72, as shown in FIG. 15. As seen in same FIG. 15, posterior piston segment 83 will carry forward guide wire 110 due to the constricting grip around guide wire 110 exerted by compressed posterior piston segment 83, as previously described for the device of FIG. 1. Guide wire 110 will enter the lumen of the vessel. As shown in FIG. 16, once posterior piston segment 83 of piston 82 will be advanced beyond the narrower segment of inner cylinder 74 of support case 70 the grip on guide wire 110 will be released due to the sudden expansion of "O" ring 85 in the anterior segment of chamber 80 of larger diameter. Guide wire 110, now loose whithin axial tract 89 of posterior piston segment 83 is no longer engaged to piston 83. At this point the operator will extract the device sliding it over guide wire 110 leaving whithin the vessel lumen a small segment of guide wire 110 over which a catheter of adequate size will be slided over, advanced and securely placed in the vessel as shown in FIG. 4. Guide wire 110, will be then extracted leaving in the vessel the catheter.

Figure 17:
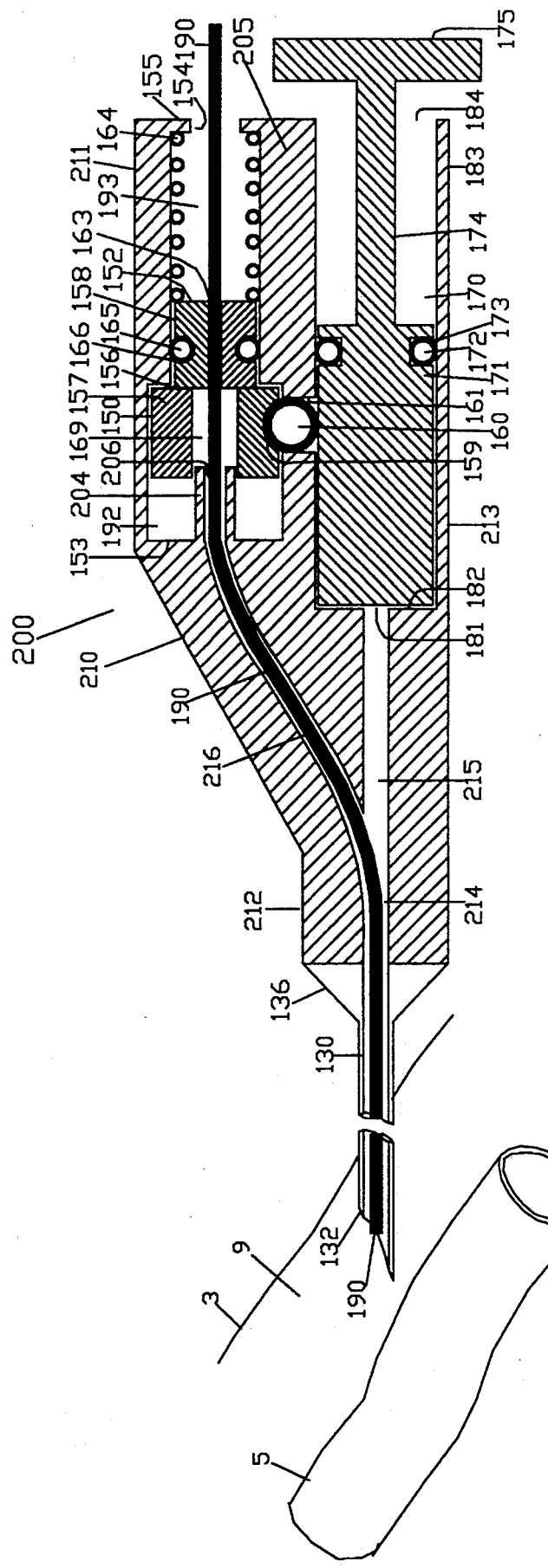
FIG. 17 is a transverse section of yet an alternative form of the device of FIG. 1, shown in an unarmed condition after skin penetration, in which a vacuum is created manually and the self propelled advancement of the guide wire is triggered automatically upon blood vessel penetration.

FIG. 17 shows another version of the device in which the vacuum is manually created by the operator and the guide wire is automatically advanced in response to blood vessel penetration. In this version the device generally indicated at 200 is composed of three main parts: hollow needle 130, guide wire 190 and support case or housing 210. Hollow needle 130 is of hollow tubular shape having tip 132 shaft 134 and hub 136. Needle hub 136 joins and fuses with anterior segment 212 of support case 210 described below.

Support case 210 is of generally cylindrical shape and it is composed of two segments, anterior 212 and posterior 213 of larger diameter. Its posterior segment 213 encloses introducer chamber 150 and vacuum chamber 170, both of general cylindrical shape, in double barrel position in respect to each other. Anterior support case or housing segment 212 has at its center conduit 214 which devices in a Y" shape fashion in upper conduit 213 reaching introducer chamber 150 via opening 206 located at posterior and of of tubular guide 204, described below, and lower conduit 215 reaching vacuum chamber 170 via opening 181.

Vacuum chamber 170 of cylindrical shape is delimited laterally by side walls 183, anteriorly by anterior wall 182 and posteriorly is open via opening 184. It contains piston 171 with "O" ring 172 seating in groove 173 and plunger 174 with T bar or handle 175. In position of rest prior to use, piston 171 is in a fully advanced position.

Introducer chamber 150 is delimited laterally by side walls 211, anteriorly by wall 153, posteriorly has opening 154 surrounded by circular flanges 155. Introducer chamber 150 is of larger diameter in its anterior segment 192 than in its posterior segment 193. Chamber 150 contains piston 156, composed of an anterior segment 157, contained in the anterior segment 192 of chamber 150 and a posterior segment 158 contained in the posterior segment 193 of chamber 150. Anterior piston segment 157, with tunnel 169 in its interior, along its longitudinal axis, has annular recess 159 for locking ball 160 contained within short conduit 161 of diaphragm or septum 205 interposed between introducer chamber 150 and vacuum chamber 170. Ball 160 seats in position of rest on side of piston 171. Tubular guide 204 for anterior piston segment 157 protrudes from wall 153 in anterior chamber 192 engaging with its most posterior segment tunnel 169 of anterior piston segment.

In position of rest, prior to use, locking ball 160 engaged on annular recess 159 of anterior piston segment 157, will not allow anterior displacement of piston 156 urged forward by spring or self propelling or advancing means 164, seating posteriorly on flanges 155 and acting upon posterior surface 152 of posterior segment 158 of piston 156. Posterior segment 158 of piston 156, as previously described for the other versions, is made of resilient, compressible material such as a rubber compound and engages guide wire 190 constricting it within axial tract 163 due to the action of "O" ring 165, seating on recess 166 of posterior piston segment 158. "O" ring 165 is made of expanding material such as steel and is constrained by the rigid walls 211 of introducer chamber 150.

Guide wire 190 loosely contained within hollow needle 130 from tip 132 to hub 136 in order to permit the passage of blood around its surface, continues within conduit 214 in anterior segment 212 of support case 210, conduit 216, tunnel 169 of anterior piston segment 157, axial tract 163 of posterior piston segment 158 and continues posteriorly exiting through opening 154 of chamber 150 to a desired length.

DESCRIPTION OF THE OPERATION

The operator will penetrate the patient skin 3 with needle tip 132 by holding the device and advancing it. Once needle tip 132 is under the skin as shown in FIG. 17, the operator will pull backward plunger 174 grabbing T bar or handle 175, creating so a vacuum in vacuum chamber 170 in front of piston 171. When needle tip 132 will penetrate a blood vessel 5 entering its lumen 7, blood will rush in chamber 170 in front of piston 171 passing through hollow needle 130 around guide wire 190 then conduit 214 and entering chamber 170 via opening 181. This will cause posterior displacement of piston 171 no longer retained in forward position by the sealing qualities of the subcutaneous tissue 9. This posterior displacement of piston-plunger 71 activates the means actuating the self propelled advancement of guide wire 190. When piston 171 will be posteriorly displaced by the action of the operator pulling on handle or T bar 175 of plunger 174 of piston 171 so that the anterior edge of piston 171 will pass beyond conduit 161, ball 160 will fall in vacuum chamber 170 in front of piston 171, allowing so the forward displacement of piston 156 urged by spring or self propelling or advancing means 64. Piston 156, no longer retained by locking ball 160. Anterior displacement of piston 156 will cause also advancing of guide wire 190 due to the grip on guide wire 190 exerted by the costriction of posterior segment piston 158 on guide wire 190 along axial tract 163. The guide wire 190 will be advanced so within the blood vessel for a length equivalent to the anterior displacement of piston 156 within introducer chamber 150. Advancement of piston 156 and guide wire 190 will stop once posterior segment of piston 158 will enter anterior segment 192 of introducer chamber 150 of larger diameter than posterior chamber 193. The sudden expansion of "O" ring 165 and resilient posterior segment 158 of piston 156 will release the grip on guide wire 190. Guide wire 190 will become loose within axial tract 163 of posterior piston segment 158 and the operator will be able to extract the device sliding it over guide wire 190 for the entire length of the guide wire. At this point a catheter will be advanced over guide wire 190 until placement within the vessel will be achieved as described for the previous device of FIG. 1 as shown in FIG. 4. The guide wire 190 will be then extracted leaving the catheter in place whithin the lumen 7 of vessel 5.

Figures 18, 18A:
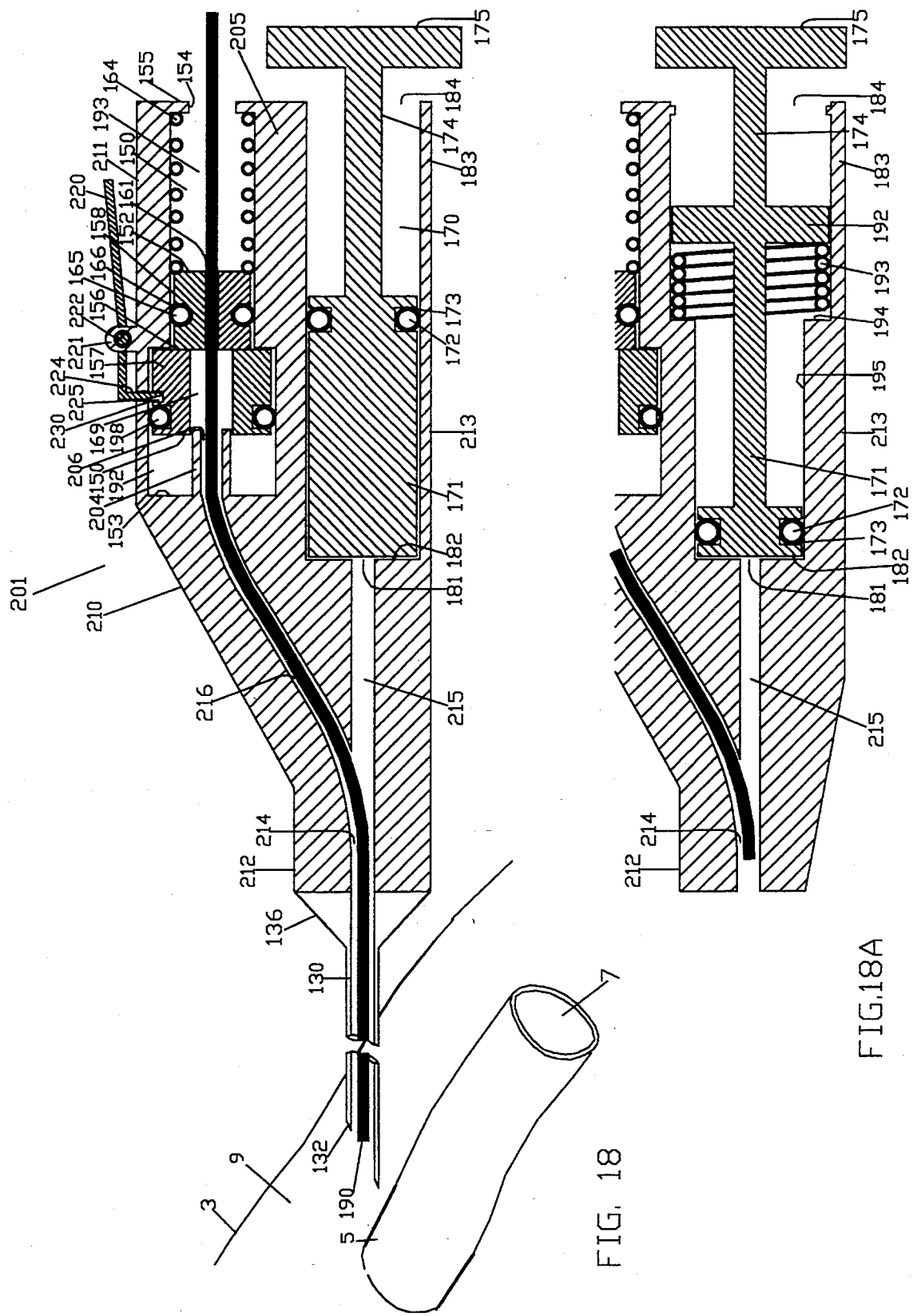
FIGS. 18 and 18A are a transverse section trough a further alternative form of the device of FIG. 1, substancially similar to the device of FIG. 17, shown after skin penetration, in which the self propelling advancement of the guide wire is triggered manually.

FIG. 18 shows an alternative form of the device described in FIG. 16 in which the vacuum is created manually as for the device of FIG. 17 but the guide wire advancement is triggered manually by the operator upon visualization of blood. In this version the device generally indicated at 201 is essentially the same as the one described in FIG. 17 with few important differences: ball 160, annular recess 159 and conduit 161 are no longer present. Triggering means or lever 220 is mounted on bridge 221 seating on superior aspect of support member 210, being 222 the fulcrum of lever 220. Tooth 224 of lever 220 in position of rest, prior to use, is engaged in opening 225 of the side wall 211 of introducer chamber 150 to reach recess 230 of anterior piston segment 157 not allowing forward motion of piston 156, urged forward as for the device of FIG. 17 by spring or advancing or self propelling means 164. The remaining parts of the device are identical to the ones described for the device of FIG. 17 except that walls 183 of vacuum chamber 170 are made of transparent material in order to visualize the presence of blood.

DESCRIPTION OF THE OPERATION

The device is operated exactly like the one described in FIG. 17, except that the guide wire advancement will be triggered manually by the operator acting upon lever 220. The operator as soon as he or she wil realize that a blood vessel 5 has been penetrated by needle tip 132 by the appearance of blood in vacuum chamber 150, he or she will release piston 156 from its resting position by pressing on posterior segment of lever 220 disengaging tooth 224 from anterior recess 230 of anterior piston segment 157. Piston 156 will be urged forward by the action of advancing or self propelling means or spring 164 as described for the device of FIG. 17. The following sequences of operation are exactly the same as the one described for the device of FIG. 17.

Figure 19:
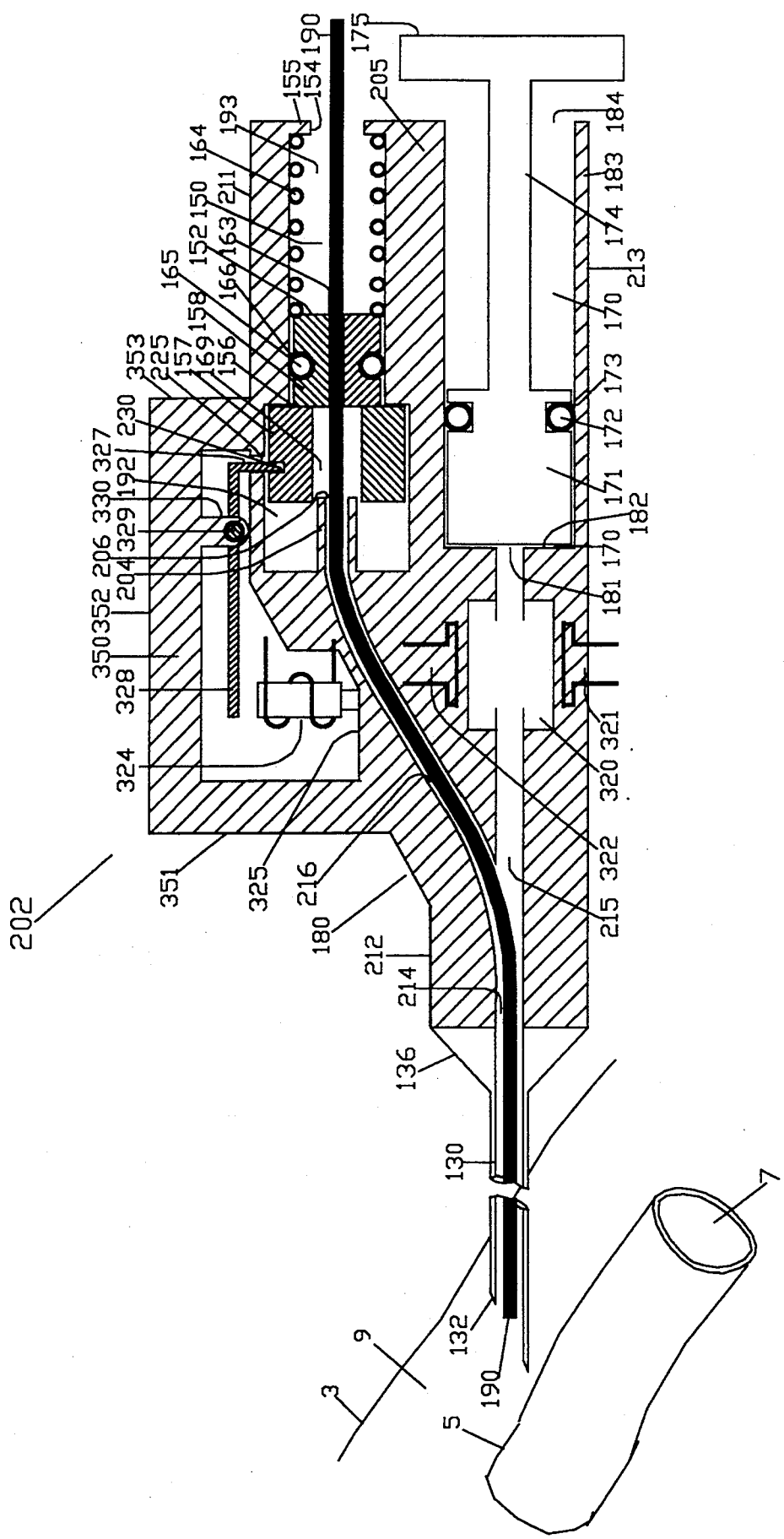
FIG. 19 shows another version of the device, shown after skin penetration, in which a vacuum is created manually, blood vessel penetration is sensed by electronic means and the guidewire advancement is triggered automatically upon blood vessel penetration.

FIG. 19 shows another version of the device in which the guide wire is advanced automatically upon penetration of the blood vessel sensed by optoelectronic means which will activate an electromagnet or solenoid via a standard known circuit.

The device generally indicated at 202, is essentially similar to the device of FIG. 18 with few important differences described below. Housing or support unit 180 has on its superior aspect lever case 350 as seen in transverse section in FIG. 19. Lever casing 350 is delimited anteriorly by wall 351, superiorly by wall 352, posteriorly by wall 353. It harbors electromagnet or solenoid 324 seating on base 325 of lever case 350.

Triggering means or lever 328 made of magnetic sensitive material is mounted with fulcrum 329 on bridge 330 solidly connected to superior wall 352 of chamber 350 of support case or housing 180. Lever 328 with tooth 327 engaged in position of rest prior to use in opening 225 reaching recess 230 on anterior piston segment 157, is tiltable on fulcrum 329 being posterior segment of lever or trigger 328 close to electromagnet 324. Within support unit 180 is contained detection chamber 320, with walls made of transparent material, and located in the middle section of conduit 215. At opposite sides of transparent detection chamber 320 are an optoelectronic emitter 321 and an optoelectronic receiver 322

DESCRIPTION OF USE

The device is operated as the previously described devices with the following differences.

As soon as needle tip 132 will be placed under the skin 3, as for all the devices previously described, the operator will pull backward plunger 174 by grabbing T bar 175, causing so a vacuum in detection chamber 320 and in chamber 170 in front of piston 171.

As soon as a blood vessel 5 will be penetrated blood will rush whithin detection chamber 320 due to the presence of vacuum. The optoelectronic sensor will activate electromagnet or solenoid 324 with resulting magnetic attraction of posterior segment of lever 328, freeing so piston 156 urged forward by advancing or self propelling means or spring 164. The following operational steps are identical to the ones described for the devices of FIGS. 17 and 18.

Figure 20:
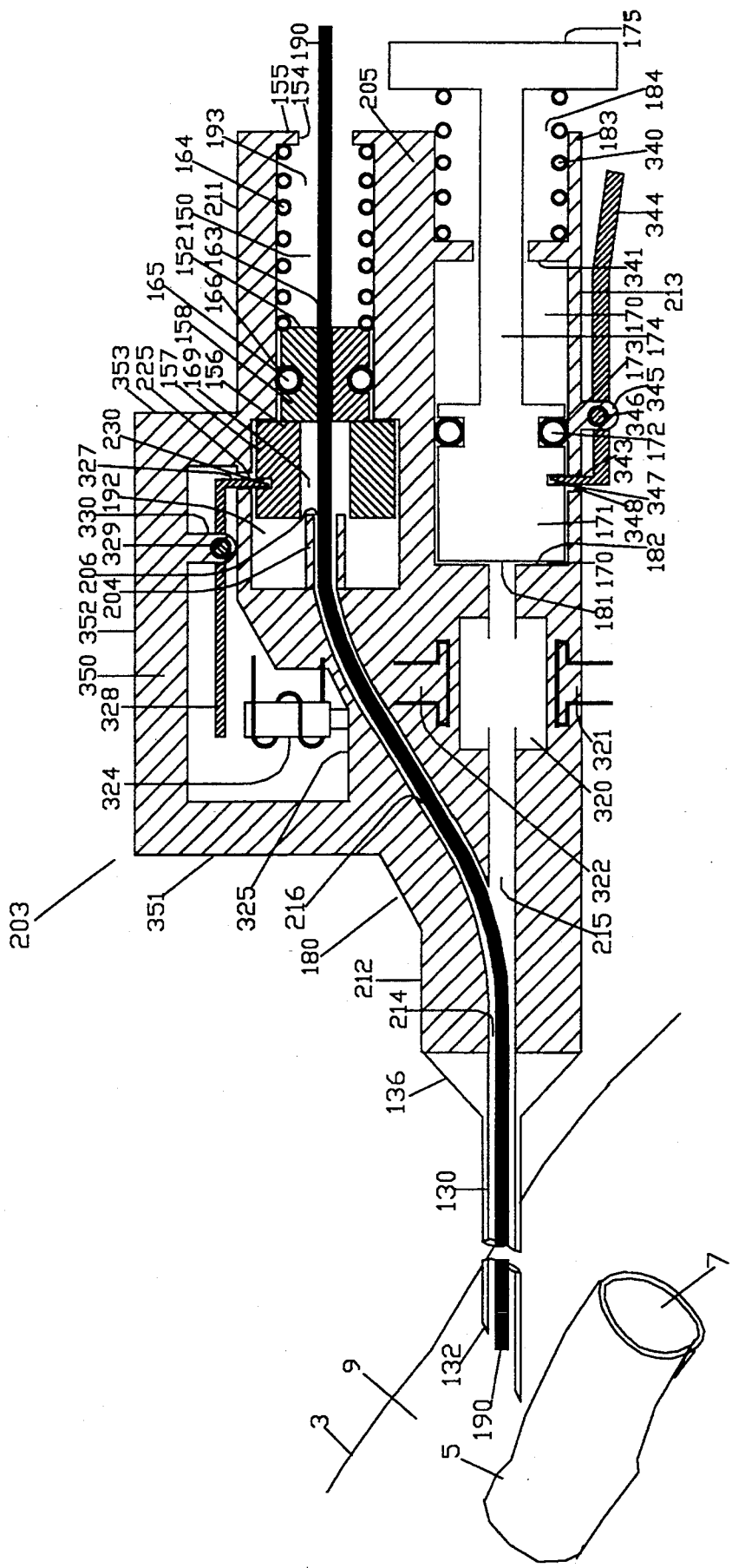
FIG. 20 shows a version similar to the device of FIG. 19 after skin penetration in unarmed condition. In this version, the vacuum is created automatically instead of manually as for the device of FIG. 19, upon blood vessel penetration.
Figure 21:
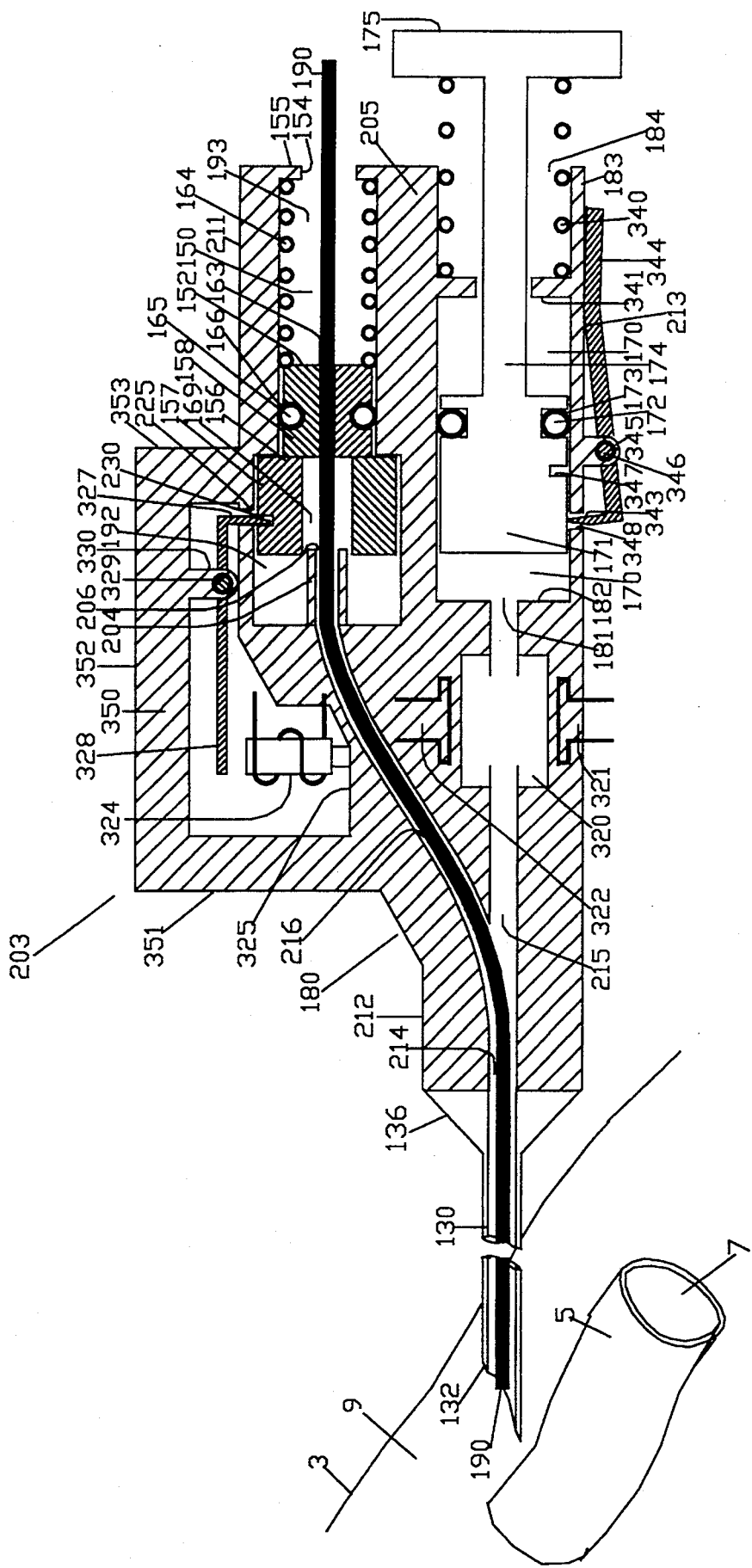
FIG. 21 shows the device of FIG. 20 in a further stage of operation, fully armed.
Figure 22:
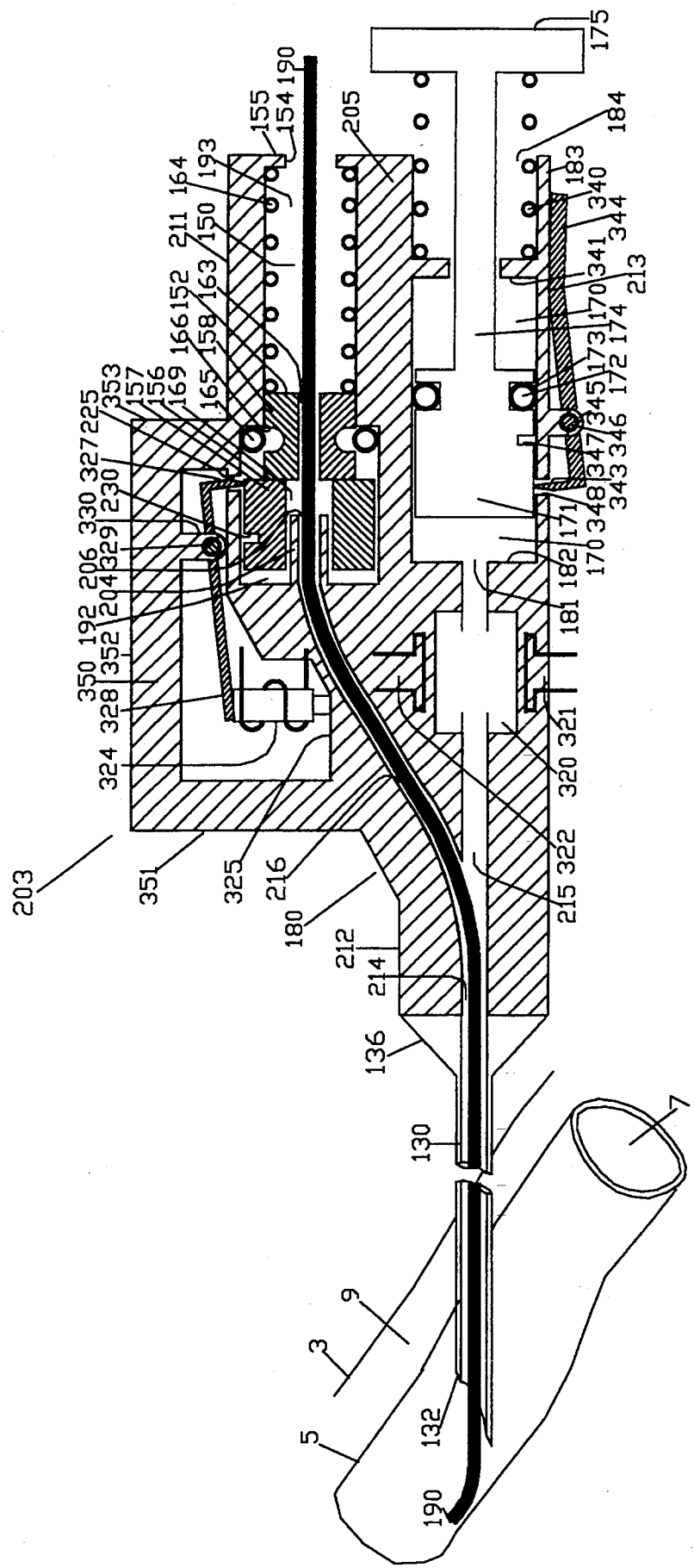
FIG. 22 shows the device of FIG. 20 in yet, a further stage of operation, in which the guide wire is advanced within the blood vessel.

FIGS. 20 to 22 describe another version of the device, generally indicated at 203, very similar to the one described in FIG. 19 with few important differences described below. Vacuum in chamber 320 and 170 is created automatically via posterior displacement of piston 171 by the extending of spring 340 seating in position of rest prior to use by the operator, between circular flanges 341, circumferentially mounted whithin interior of chamber 171 and T bar 175 of plunger 174. Piston 171 is locked prior to use in position of rest in advanced position whithin chamber 171 by tooth 343 of lever 344 mounted via fulcrum 345 on bridge 345 of support case 210, engaged in recess 347 of piston 171 via passing trough opening 348 of support unit 180. The rest of the device is exactly the same as the device described in FIG. 19.

DESCRIPTION OF THE OPERATION

The device is operated essentially in the same manner as the device of FIG. 19, with the difference that once the patient skin 3 has been penetrated by needle tip 132 the operator will press upon lever 344 as shown in FIG. 21, allowing so piston 171 to be displaced backward by the extension of spring 340 as shown in FIG. 21. This will create a vacuum in detection chamber 320. As shown in FIG. 22 when a blood vessel will be penetrated blood will rush within detection chamber 320. The optoelectric pair will sense blood presence and this will activate electromagnet 324. Piston 156 will be allowed to move forward by the disengaging of tooth 230 from recess 225 of piston 156. The following sequences are exactly the same as the ones described for the previously described devices. The light emitting source and the light sensor can both be placed in the same side of the detection chamber 320. In this case the light sensor will detect a beam reflected from the opposite side. Blood will acts as reflecting or diffusing medium. FIGS. 23 to 29 describe schematically various type of sensors employed for the detection of the blood in chamber 320 upon blood vessel penetration and the activation of the guide wire advancement mechanism. Activation of electromagnet 324 is the same for all the described sensing mechanism, via one of the known standard circuits.

Figure 23:
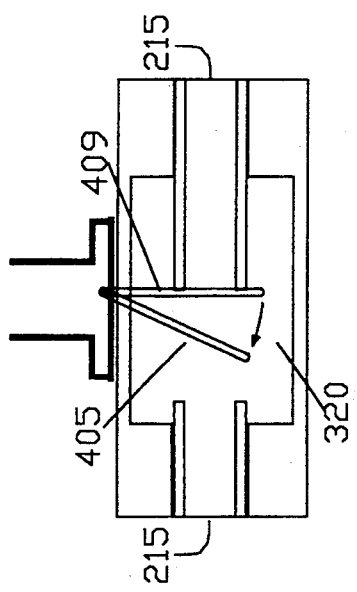
FIG. 23 is an enlargement of the detection chamber of FIG. 19, showing in it temperature sensors.

FIG. 23 shows temperature sensors which sense the occurred penetration of the blood vessel by detecting the variation of temperature induced on temperature sensors 400 and 402 by the blood rushing in chamber 320.

Figure 24:
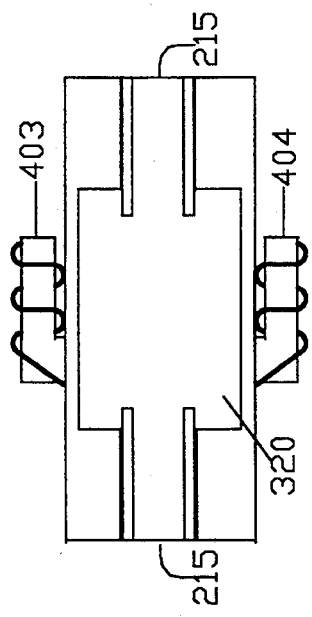
FIG. 24 is an enlargement of the detection chamber of FIG. 19, showing in it sensors detecting the electrical properties of the blood.

FIG. 24 shows sensors 403 and 404 which detect the phisical properties of conductivity of the blood. Blood rushing in detection chamber 324 upon blood vessel penetration is detected by the application of the principle that a voltage proportional to the rate of flow is induced in a conductor moving through a magnetic field at right angle to the magnetic lines of forces.

Figure 25:
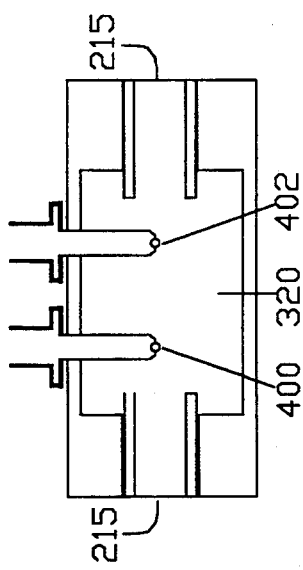
FIG. 25 is an enlargement of the detection chamber of Fig. 19 showing in it a flow sensor.

FIG. 25 shows flow sensing element 405 tiltable on pivot 409. Its angular displacement due to the flowing of blood in chamber 320 will activate electromagnet 324.

Figure 26:
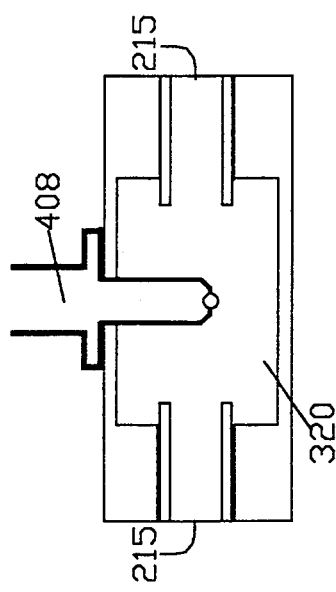
FIG. 26 is an enlargement of the detection chamber of FIG. 19, showing in it an acoustic sensor.

FIG. 26 shows sensor 406 detecting static and dynamic acoustic properties of the blood. Sensors based on ultrasound/sonar detection are also included.

Figure 27:
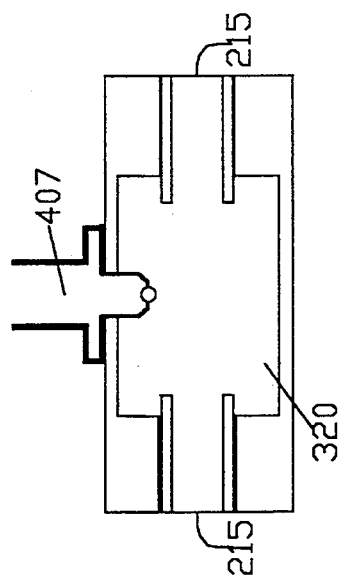
FIG. 27 is an enlargement of the detection chamber of FIG. 19, showing in it a pressure sensor.

FIG. 27 shows sensor 407, which is a pressure/vacuum transducer. Such sensor will activate electromagnet 324 upon arrival of blood in chamber 320, detecting pressure changes in chamber 320.

Figure 28:
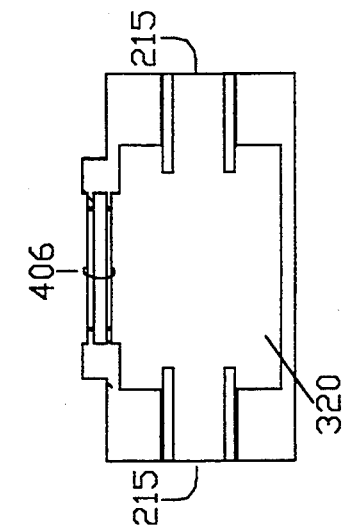
FIG. 28 is an enlargement of the detection chamber of FIG. 19, showing in it a sensor detecting the chemical properties of the blood or its components.

FIG. 28 is a schematic representation of a sensor, 408, able to detect the chemical properties of the blood, such as certain ranges of pH, or able to detect blood components by analysis.

What we claim is:

1. A guidewire placement device for insertion of guidewire into the interior of a vessel, comprising:
    a guidewire;
    a hollow needle, said guidewire passing through said hollow needle;
    self-propelling means for advancement of the guidewire into the interior of a vessel upon penetration of said hollow needle into the vessel.

2. The device of claim 1 wherein: said self-propelling means is resilient.

3. The device of claim 1 wherein: said self-propelling means is expandable material.

4. The device of claim 1 wherein: said self-propelling means is pneumatic.

5. The device of claim 1 wherein: said self-propelling means is magnetic.

6. The device of claim 1 wherein: said self-propelling means for the guidewire advancement is actuable in response to penetration of a blood vessel by said needle.

7. The device of claim 1 wherein: said self-propelling means for the guidewire advancement is manually actuable.

8. The device of claim 1 wherein: said self-propelling means for the guidewire advancement is automatically actuable in response to blood vessel penetration.

9. The device of claim 1 further comprising:
    means for identifying penetration of a blood vessel by said hollow needle.

10. The device of claim 1 further comprising:
    means for sensing penetration of a blood vessel by said hollow needle.

11. The device of claim 10 wherein: said means for sensing penetration of a blood vessel by said needle includes:
    means sensing fall of resistance to forward pressure exerted upon said guidewire by said self-propelling means, occurring upon blood vessel penetration of said hollow needle carrying said guidewire.

12. The device of claim 11, wherein: said means sensing fall of resistance to forward pressure exerted upon said guidewire comprises:
    propelling means urging said guidewire forward against the resistance of the tissues interposed between the skin and the vessel once the needle carrying said guidewire has penetrated the skin.

13. The device of claim 11, wherein: said means sensing fall of resistance to forward pressure exerted upon said guidewire actuates means to induce an automatic advancement of said guidewire inside the penetrated vessel.

14. The device of claim 11, wherein: said means sensing fall of resistance comprises:
resilient means urging a piston member of resilient compressible material slideable within a chamber, said chamber composed of a narrowed segment continuing into a contiguous expanded segment, said piston member encircling a portion of the guidewire and being constrained to a status of compression around said guidewire with resulting grip upon the guidewire to engage said guidewire while said member is sliding within the narrowed segment of its chamber, said piston member of resilient material being encircled by an annular structure of resilient material of relatively low friction properties so to enhance the slideability of said member within said chamber, with resulting advancement of the guidewire into a blood vessel, said piston member then expanding when passing into the contiguous expanded segment of the chamber due to the resiliency of its material, with resulting release of its grip on the guidewire to disengage said guidewire.

15. The device of claim 10 wherein said means for sensing penetration of a blood vessel by said needle includes:
means for sensing pressure differential, occurring upon blood vessel penetration, between the pressure inside the blood vessel and the pressure within a chamber communicating with said hollow needle.

16. The device of claim 15 wherein:
said means for sensing pressure differential includes a chamber communicating with said hollow needle in which chamber the pressure is less than the pressure within a blood vessel.

17. The device of claim 16 wherein said chamber is a vacuum chamber.

18. The device of claim 15 wherein said means for sensing pressure differential includes:
means for creation of a pressure, within said chamber, below the pressure present within the penetrated blood vessel.

19. The device of claim 15 wherein said means for sensing pressure differential includes:
means for creation of a vacuum within said chamber.

20. The device of claim 19 wherein said means for creation of said vacuum comprises:
a slideable piston contained within said chamber.

21. The device of claim 20 wherein said piston slideable within said chamber creates a vacuum by means of rearward displacement.

22. The device of claim 21 wherein said rearward displacement of said slideable piston is accomplished manually.

23. The device of claim 21 wherein said rearward displacement of said slideable piston is accomplished automatically by resilient means.

24. The device of claim 19 wherein said means for creation of said vacuum comprises:
a cap airtightly closing the open end of a chamber, said cap being slideable over the sidewalls of said chamber to expand the volume of the chamber to create vacuum within the chamber, said chamber being in communication with said hollow needle.

25. The device of claim 19 further comprising:
means for arming said means for creation of a vacuum.

26. The device of claim 15 further comprising:
means for arming said means for sensing pressure differential.

27. The device of claim 10 further comprising:
means for manual actuation of said means for self-propelled advancement of said guidewire upon activation of said sensing means.

28. The device of claim 10 further comprising:
means for automatic actuation of said means for self-propelled advancement of said guidewire upon activation of said sensing means.

29. The device of claim 10 wherein: said means for sensing penetration comprises:
optical sensing means.

30. The device of claim 10 wherein said means for sensing penetration comprises:
temperature sensing means 31. The device of claim 10 wherein: said means for sensing penetration comprises:
means for sensing electrical properties of the blood.

32. The device of claim 10 wherein: said means for sensing penetration comprises:
means for detecting the physical properties of the blood as a fluid.

33. The device of claim 10 wherein: said means for sensing penetration comprises:
acoustic sensing means.

34. The device of claim 10 wherein: said means for sensing penetration comprises:
ultrasounds sensing means.

35. The device of claim 10 wherein said means for sensing penetration comprises:
pressure sensing means.

36. The device of claim 10 wherein said means for sensing penetration comprises:
means for detecting chemical properties of the blood.

37. The device of claim 10 wherein said means for sensing penetration comprises:
means for identifying blood by detecting blood components.

38. The device of claim 10 wherein said means for sensing penetration actuates an electromagnet to automatically advance said guidewire.

39. The device of claim 10 further comprising:
means for arming said means for sensing penetration of a blood vessel.

40. The device of claim 39, wherein said means for arming said means for sensing penetration of a blood vessel comprises:
a piston-plunger provided with a handle for manual arming by rearward displacement of the piston-plunger, said piston-plunger airtightly sliding within a vacuum chamber to create a vacuum so to permit blood rushing into said vacuum chamber upon penetration of a blood vessel alerting the operator to actuate the self-propelling means for the advancement of the guidewire.

41. The device of claim 39, wherein said means for arming said means for sensing penetration of a blood vessel comprises:
an arming member, slideable on the sidewalls of a chamber housing propelling means, said slideable arming member having means for releasable engagement to said chamber in a retracted resting position and means for engagement to said chamber in an advanced arming position, said arming member having also means to retain the rear end of said resilient means when the slideable member is advanced to a forward position to arm said propelling means.

42. The device of claim 39, wherein said means for arming said means for sensing penetration of a blood vessel comprise:
means to manually rearwardly displace a vacuum cap said vacuum cap thereafter being urged forward by resilient means loaded by said manual rearward displacement, said vacuum cap airtightly closing the open end of a chamber, said vacuum cap being also slideable over the sidewalls of said chamber to expand the volume of said chamber to create vacuum within said chamber until, upon blood vessel penetration of said hollow needle, blood is permitted to enter the vacuum chamber, with consequent vanishing of the vacuum.

43. The device of claim 1 further comprising:
means actuating said means for self-propelled advancement of said guidewire.

44. The device of claim 43 wherein said actuating means is manually operable.

45. The device of claim 44 wherein said manually operable actuating means comprises:
a manually operable lever provided with a retaining tooth, releasably retaining in a rearward position a piston to which said guidewire is releasably engaged, said piston being urged forward by said self-propelling means and self-propelled to an advanced position upon manual displacement of said lever.

46. The device of claim 43 wherein said actuating means is automatically (activated) actuable in response to blood vessel penetration.

47. The device of claim 46 wherein said automatically activated means actuating said self-propelling means for the advancement of said guidewire comprises:
a ball member mounted in a window formed in a piston casing, said ball member protruding from said window into a corresponding annular recess formed in a piston slideable within said casing, thus releasably engaging said slideable piston to said piston casing, said ball member being releasably retained inside said window of the piston casing and into said annular recess of the piston by the wall of a slideable vacuum cylinder over said piston casing, said ball member being then released following displacement of the wall of said slideable vacuum cylinder with resulting unlocking of said piston from said piston casing and actuating said self-propelling means forwardly urging said piston releasably engaging said guidewire.

48. The device of claim 46 wherein said automatically actuable means actuating said self-propelling means for the advancement of said guidewire comprises:
a ball member
a round window formed in a lateral wall of a piston casing, said round window housing said ball, said lateral wall of said piston casing being of an overall thickness greater than the radius of said ball and smaller than its diameter,
an annular recess formed in a piston slideable within said piston casing, said annular recess being of such depth that when said annular recess of said piston is aligned with the round window of said piston casing, and the ball housed in said round window seats in said annular recess with one of its pole, the opposite pole of said ball is leveled with the outer surface of the wall of said piston casing,
a generally cylindrical member, slideable over said piston casing along said outer surface of the wall of said piston case, with slideable lateral walls sufficiently rigid to keep the ball, said ball being seated in the annular recess of the piston and being housed in the round window of the wall of said piston casing, from being ejected outwardly by the propelling means urging said piston forward and therefore urging the ball to step out of the annular recess to level its inner pole with the surface of the piston, said ball being retained within said round window by said rigid lateral walls of said generally cylindrical member slideable over the piston casing releasably locks said piston to its piston casing, said lateral walls of said generally cylindrical member slideable over the piston casing are of such length that at a predetermined stage of advancement of said member, said lateral walls, by no longer overlaying on said ball, will expose the ball, therefore will, by no longer retaining the ball, seating in the annular recess of the piston, allows the ball to be ejected out of said annular recess and to level its inner pole with the lateral surface of said piston, permitting, in so doing, to unlock the piston from the piston casing.

49. The device of claim 46 wherein: said automatically actuable means actuating said self-propelling means for the advancement of said guidewire comprises:
a ball member mounted in a conduit formed in a septum separating an introducer chamber from a parallel vacuum chamber, said introducer chamber containing a piston releasably engaging the guidewire, and said vacuum chamber containing a vacuum creating piston-plunger, said ball member in said conduit releasably locking the piston of the introducer chamber by protruding from said conduit into an annular recess formed in said piston of the introducer chamber, said ball member being retained in said annular recess by the piston plunger of said vacuum chamber, said ball member then unlocking the piston of the introducer chamber, being no longer retained in the annular recess of the piston of the introducer member by the rearwardly displaced piston-plunger of the vacuum chamber, the unlocking of the piston of the introducer chamber results in an advancement of the guidewire, being said piston releasable engaged to the guidewire.

50. The device of claim 46 wherein said automatically activated means actuating said self-propelling means for the advancement of said guidewire comprises:
a lever provided with a retaining tooth releasably retaining a piston, to which said guidewire is releasably engaged, by engagement of said tooth into a recess formed in said piston, said piston being urged forward by said self-propelling means, said lever being displaceable by an electromagnet activated in response to blood vessel penetration.

51. The device of claim 1 wherein said self-propelling means advances said guidewire acting upon means releasably engaging said guidewire.

52. The device of claim 51 wherein said means releasably engaging said guidewire is
a piston member of resilient compressible material slideable within a chamber composed of a narrowed segment continuing into a contiguous expanded segment, said piston member encircling a portion of the guidewire and being constrained to a status of compression around said guidewire with resulting grip upon the guidewire to engage said guidewire while said piston member is sliding within the narrowed segment of its chamber, said piston member then expanding when passing into the contiguous expanded segment of the chamber due to the resiliency of its material with resulting release of its grip on the guidewire to disengage said guidewire.

53. The device of claim 52 wherein said piston member of resilient material encircling the guidewire is encircled as well by an annular structure of resilient material of relatively low friction properties so to enhance the slideability of said member within said chamber.

54. The device of claim 51 wherein said means releasably engaging said guidewire is
a gripping unit composed of multiple resilient arms longitudinally protruding from a piston base member slideable within a chamber constructed with a restrained segment continuing into a contiguous expanded segment, said gripping unit having a bore along its central longitudinal axis for the passage of said guidewire and said protruding arms being constrained centripetally to compress said guidewire with resulting clamping action upon the guidewire to engage said guidewire while said gripping unit is sliding within the narrowed segment of its chamber, said arms then allowed to release their clamping action upon the guidewire when said gripping unit passes into the contiguous expanded segment of the chamber with resulting disengagement of said guidewire from said gripping unit.

55. The device of claim 51 wherein said means releasably engaging said guidewire is an adapted jaw chuck with multiple jaws radially mounted in a supporting piston member slideable within a chamber constructed with a narrowed segment continuing into a contiguous expanded segment, said supporting piston member having a bore along its central longitudinal axis for the passage of said guidewire and said jaws being constrained centripetally to compress said guidewire with resulting clamping action upon the guidewire to engage said guidewire while said piston member is sliding within the restrained segment of its chamber, said jaws then allowed to release their clamping action upon the guidewire when said piston member passes into the contiguous expanded segment of the chamber with resulting disengagement of said guidewire from said jaws chuck.

56. The device of claim 1 further comprising:
means for arming said means for self-propelled advancement of said guidewire.

57. The device of claim 56, wherein said means for arming said means for self-propelled advancement of the guidewire into a blood vessel comprises:
a piston-plunger provided with a handle for manual arming by rearward displacement of the piston-plunger, said piston-plunger airtightly sliding within a vacuum chamber to create a vacuum so to permit blood rushing into said vacuum chamber upon penetration of a blood vessel with consequent further rearward displacement of the piston-plunger to a point where means for actuation of self-propelled means for the advancement of the guidewire are automatically activated.

58. The device of claim 56, wherein said means for arming said means for self-propelled advancement of the guidewire into a blood vessel comprises:
a piston-plunger provided with a handle for manual arming by rearward displacement of the piston-plunger, said piston-plunger airtightly sliding within a vacuum chamber to create a vacuum so to permit blood rushing into said vacuum chamber upon penetration of a blood vessel, said blood being detected by sensors to automatically actuate said self-propelling means.

59. The device of claim 56, wherein: said means for arming said means for self-propelled advancement of the guidewire into a blood vessel comprises:
a retaining lever mounted on the walls of a vacuum chamber, locking a piston-plunger slideable within said chamber, with a retaining tooth engaged into a correspondent recess formed in the piston-plunger and
resilient means acting upon said piston-plunger urging said piston-plunger to withdraw from its advanced resting position to create a vacuum in front of said-piston plunger, upon disengagement of the lever from said piston-plunger.

60. The device of claim 16 further comprising:
means for arming said means for creation of a pressure, within said chamber, below the pressure inside the penetrated blood vessel.

61. A guidewire placement device for insertion of guidewire into the interior of a vessel, comprising:
(a) a guidewire,
(b) means for self-propelled advancement of said guidewire into a vessel,
(c) a hollow needle having a tip,
(d) a housing for said means for self-propelled advancement of the guidewire, said hollow needle being in communication with said housing, said guidewire passing through said housing and said needle up to the tip.

62. A guidewire placement device for insertion of guidewire into the interior of a vessel, comprising:
(a) a housing;
(b) a hollow needle in communication with the housing, the needle having a tip;
(c) a guidewire passing through the housing into the needle and up to the needle tip; and
(d) means within the housing for self-advancing the guidewire into the interior of the vessel upon penetration of the needle tip into the interior of the vessel.

63. The guidewire placement device of claim 62 wherein the advancing means further comprises a releasable guidewire gripping means.

64. The guidewire placement device of claim 63 wherein the gripping means is adapted to release the guidewire after the guidewire has advanced a predetermined amount afterwhich the needle and housing may be removed from the guidewire.

65. The guidewire placement device of claim 62, further comprising trigger means for actuation of the gripping means to advance the guidewire.

66. The guidewire placement device of claim 62 wherein the advancing means comprises a spring.

67. The guidewire placement device of claim 62 wherein the advancing means comprises compressed air.

68. The guidewire placement device of claim 62, further comprising a vacuum means within the housing to draw a fluid from the interior of the vessel into the housing.

69. The guidewire placement device of claim 67, further comprising a sensing means to determine if the fluid is in the housing.

70. A guidewire placement device for insertion of a guidewire into the interior of a vessel, comprising:
(a) a housing including a vacuum chamber,
(b) a hollow needle in communication with said vacuum chamber,
(c) a guidewire slideable within said hollow needle, and
(d) means for advancing said guidewire, said vacuum chamber accelerating a backflow of blood toward said housing upon blood vessel penetration, said guidewire being advanceable through said needle into said blood vessel upon blood vessel penetration.

71. A guidewire placement device for insertion of a guidewire into the interior of a blood vessel, comprising:
a housing including a vacuum enclosure,
a hollow needle in flow communication with said vacuum enclosure, said needle having a tip,
a guidewire entering said vacuum enclosure, and
a sealing means, said sealing means sealing to the housing the guidewire entering said vacuum enclosure,
a vacuum pressure being formed in said vacuum enclosure upon tissues sealing of the needle tip occurring upon penetration of said needle tip into tissues overlaying said blood vessel said vacuum pressure accelerating a backflow of blood toward said vacuum enclosure upon blood vessel penetration of said needle tip, said guidewire being advanceable through said needle into said blood vessel upon blood vessel penetration.

72. The guidewire placement device of claim 71 wherein said vacuum enclosure comprises:
a vacuum chamber.

73. A guidewire placement device for insertion of a guidewire into the interior of a blood vessel, comprising:
a housing adapted to receive passage of a guidewire, said housing including a vacuum enclosure,
a hollow needle in flow communication with said vacuum enclosure, said needle having a tip, said hollow needle having a sufficient internal diameter to allow passage of said guidewire,
a sealing means, said sealing means being adapted to seal to the housing a guidewire slideable into said vacuum enclosure through said sealing means,
a vacuum pressure being generated in said vacuum enclosure upon sliding of said guidewire into said vacuum enclosure through said sealing means and upon tissues sealing of the needle tip occurring upon penetration of said needle tip into tissues overlaying said blood vessel, said vacuum pressure accelerating a backflow of blood toward said vacuum enclosure upon blood vessel penetration of said needle tip, said guidewire being advanceable through said needle into said blood vessel upon blood vessel penetration.

74. A guidewire placement device for insertion of a guidewire into the interior of a blood vessel, comprising:
a hollow needle, said needle having a tip for penetration into a blood vessel, said hollow needle having a sufficient internal diameter to allow passage of a guidewire,
a housing having an interior passageway in flow communication with said hollow needle, said passageway being adapted to receive passage of said guidewire, said housing having also a conduit in flow communication with said passageway, said conduit having an opening to the exterior,
at least one sealing member, said sealing member being adapted to provide a sealing of the passageway around said guidewire, said sealing member preventing backflow of blood into the passageway beyond the sealing member, from a blood vessel penetrated by said needle.

75. A guidewire placement device for insertion of a guidewire into the interior of a blood vessel, comprising:
a hollow needle, said needle having a tip for penetration into a blood vessel, said hollow needle having a sufficient internal diameter to allow passage of a guidewire,
a housing having an interior passageway in flow communication with said hollow needle, said passageway being adapted to receive passage of said guidewire, said housing having also a conduit in flow communication with said passageway, said conduit having an opening for connection to a vacuum creating means,
at least one sealing member, said sealing member being adapted to provide a sealing of the passageway around said guidewire, said sealing member preventing backflow of blood into the passageway beyond the sealing member, from a blood vessel penetrated by said needle.

76. The guidewire placement device of claim 75 wherein said guidewire tip laying within the needle is positioned in near proximity of the needle tip.

77. A guidewire placement device for insertion of a guidewire into the interior of a blood vessel, comprising:
a hollow needle, said needle having a tip for penetration into a blood vessel, said hollow needle having a sufficient internal diameter to allow passage of a guidewire,
a housing having an interior passageway in flow communication with said hollow needle, said passageway being adapted to receive passage of said guidewire, said housing having also a conduit in flow communication with said passageway, said conduit having an opening to the exterior,
at least one sealing member, said sealing member being adapted to provide a sealing of the passageway around said guidewire, said sealing member preventing backflow of blood into the passageway beyond the sealing member, from a blood vessel penetrated by said needle,
a guidewire having a tip, said guidewire tip laying within the needle upon needle insertion into body tissues to allow prompt engagement of the guidewire tip into the blood vessel upon needle tip penetration of the blood vessel, said engagement of the tip of the guidewire into the blood vessel being actuable by a guidewire advancement of an amount shorter than the length of the needle.

78. The guidewire placement device of claim 76 wherein said guidewire tip laying within the needle is positioned in near proximity of the needle tip.

79. A guidewire placement device for insertion of a guidewire into the interior of a blood vessel, comprising:
- a hollow needle, said needle having a tip for penetration into a blood vessel, said hollow needle having a sufficient internal diameter to allow passage of a guidewire,
- a housing having an interior passageway in flow communication with said hollow needle, said passageway being adapted to receive passage of said guidewire, said housing also a conduit in flow communication with said passageway, said conduit having an opening for connection to a vacuum creating means,
- at least one sealing member, said sealing member being adapted to provide a sealing of the passageway around said guidewire, said sealing member preventing backflow of blood into the passageway beyond the sealing member, from a blood vessel penetrated by said needle
- a guidewire having a tip, said guidewire tip laying within the needle upon needle insertion into body tissues to allow prompt engagement of the guidewire tip into the blood vessel upon needle tip penetration of the blood vessel, said engagement of the tip of the guidewire into the blood vessel being actuable by a guidewire advancement of an amount shorter than the length of the needle.

80. A guidewire placement device for insertion of a guidewire into the interior of a blood vessel, comprising:
- (a) a housing including a vacuum chamber for vacuum pressure,
- (b) a hollow needle in communication with said vacuum chamber,
- (c) a guidewire slideable within said hollow needle, and
- (d) means for advancing said guidewire, said vacuum pressure vanishing upon penetration of said blood vessel by said needle, said guidewire being advanceable through said needle into said vessel upon the vanishing of said vacuum pressure.

81. A guidewire placement device for insertion of a guidewire through a wall of a body cavity of a patient, comprising:
- (a) a housing including a vacuum chamber for vacuum pressure,
- (b) a hollow needle in communication with said vacuum chamber,
- (c) a guidewire slideable within said hollow needle, and
- (d) means for advancing said guidewire, said vacuum pressure vanishing upon penetration of said body cavity by said needle, said guidewire being advanceable through said needle into said cavity upon the vanishing of said vacuum pressure.

* * * * *